US009696275B2

(12) United States Patent
Gillis et al.

(10) Patent No.: US 9,696,275 B2
(45) Date of Patent: Jul. 4, 2017

(54) ADDRESSABLE ELECTRODE ARRAYS IN MULTIPLE FLUIDIC COMPARTMENTS AND USES THEREOF

(71) Applicant: The Curators of the University of Missouri, Columbia, MO (US)

(72) Inventors: Kevin Gillis, Columbia, MO (US); Jia Yao, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 487 days.

(21) Appl. No.: 14/052,394

(22) Filed: Oct. 11, 2013

(65) Prior Publication Data
US 2014/0106988 A1 Apr. 17, 2014

Related U.S. Application Data

(60) Provisional application No. 61/713,408, filed on Oct. 12, 2012.

(51) Int. Cl.
| | | |
|---|---|---|
| G01F 1/64 | (2006.01) | |
| G01N 27/00 | (2006.01) | |
| G01N 27/417 | (2006.01) | |
| G01N 27/27 | (2006.01) | |

(52) U.S. Cl.
CPC .......... *G01N 27/417* (2013.01); *G01N 27/27* (2013.01)

(58) Field of Classification Search
CPC .................................. G01F 1/64; G01N 27/00
USPC ...... 422/68.1, 82.01; 436/43, 149, 150, 151; 205/775
See application file for complete search history.

(56) References Cited

U.S. PATENT DOCUMENTS

| | | | |
|---|---|---|---|
| 7,456,012 B2 | 11/2008 | Ryttsen et al. | |
| 8,232,074 B2 | 7/2012 | Jardemark et al. | |
| 2001/0029320 A1* | 10/2001 | Trumbull et al. ............. | 600/300 |
| 2002/0182627 A1* | 12/2002 | Wang et al. ...................... | 435/6 |
| 2004/0182707 A1* | 9/2004 | Jardemark et al. ........... | 204/451 |
| 2006/0003310 A1 | 1/2006 | Klauke et al. | |
| 2007/0155016 A1* | 7/2007 | Lee et al. ....................... | 435/461 |
| 2009/0283425 A1* | 11/2009 | Clark et al. ................... | 205/792 |
| 2010/0129856 A1 | 5/2010 | Fang et al. | |
| 2012/0190583 A1 | 7/2012 | Gillis et al. | |
| 2013/0140191 A1* | 6/2013 | Unwin et al. .............. | 205/790.5 |

FOREIGN PATENT DOCUMENTS

| | | |
|---|---|---|
| WO | 2009073121 A1 | 6/2009 |
| WO | 2010027446 A2 | 3/2010 |

OTHER PUBLICATIONS

Amatore et al., "Coupling of Electrochemistry and Fluorescence Microscopy at Indium Tin Oxide Microelectrodes for the Analysis of Single Exocytotic Events", Angewandte Chemie—International Edition, 2006, pp. 4000-4003, vol. 45.
Amatore et al., "Relationship Between Amperometric Pre-Spike Feet and Secretion Granule Composition in Chromaffin Cells: An Overview", Biophysical Chemistry, 2007, pp. 181-189, vol. 129.
(Continued)

*Primary Examiner* — Brian J Sines
(74) *Attorney, Agent, or Firm* — Thompson Coburn, LLP; Thaddeus J. Blenke

(57) ABSTRACT

Methods and apparati for performing measurements of electrical signals in a multi-compartmented fluidic array format where the signal to noise ratio is improved are disclosed.

17 Claims, 12 Drawing Sheets

(56) References Cited

OTHER PUBLICATIONS

Anne et al., "Optimizing Electrode-Attached Redox-Peptides Systems for Kinetic Characterization of Protease Action on Immobilized Substrates. Observation of Dissimilar Behavior of Trypsin and Thrombin Enzymes", Langmuir, 2012, pp. 8804-8813, vol. 28 Issue 23.
Barbour et al., "Combining Loose Cell-Attached Stimulation and Recording", Journal of Neuroscience Methods, 2000, pp. 199-208, vol. 103.
Bard et al., Electrochemical Methods: Fundamentals and Applications, 2001, Wiley & Sons, New York.
Barizuddin et al., "Automated Targeting of Cells to Electrochemical Electrodes Using a Surface Chemistry Approach for the Measurement of Quantal Exocytosis", ACS Chemical Neuroscience, 2010, pp. 590-597, vol. 1.
Barizuddin, "Self-Aligned Microchip Device for Automated Measurement of Quantal Exocytosis", Doctoral Thesis for University of Missouri-Columbia, 2010, pp. 1-193.
Berberian et al., "Improved Surface-Patterned Platinum Microelectrodes for the Study of Exocytotic Events", Analytical Chemistry, 2009, pp. 8734-8740, vol. 81.
Yao et al.,"A Novel Multiplexing Approach for Individually Addressable Electrode Arrays with Reduced External Connections", Poster presented at the Biomedical Engineering Society annual meeting, Oct. 12-15, 2011, Hartford, CT, www.bmes.org.
Yao et al.,"A Multiplexed Electrochemical Electrode Array for High Throughput Measurements of Quantal Exocytosis", Poster presented at the Biophysical Society annual meeting, Mar. 5-9, 2011, Baltimore, MD, www.biophysics.org.
Cahill et al., "Simultaneous Amperometric Measurement of Ascorbate and Catecholamine Secretion from Individual Bovine Adrenal Medullary Cells", Analytical Chemistry, Aug. 1, 1995, pp. 2599-2605, vol. 67, No. 15.
Chen et al., "Amperometric Detection of Quantal Catecholamine Secretion from Individual Cells on Micromachined Silicon Chips", Analytical Chemistry, 2003, pp. 518-524, vol. 75.
Chen et al., "Controlled On-Chip Stimulation of Quantal Catecholamine Release from Chromaffin Cells Using Photolysis of Caged Ca2+ on Transparent Indium-Tin-Oxide Microchip Electrodes", Lab on a Chip—Miniaturisation for Chemistry and Biology, 2008, pp. 161-169, vol. 8.
Cheng, "Monitoring Single Heart Cell Biology using Lab-on-a-Chip Technologies", A Thesis Submitted for the Degree of Doctor of Philosophy at the University of Glasgow, Mar. 2009, pp. 1-173.
Chow et al., "Delay in Vesicle Fusion Revealed by Electrochemical Monitoring of Single Secretory Events in Adrenal Chromaffin Cells", Nature, 1992, pp. 60-63, vol. 356.
Dias et al., "An Electrochemical Detector Array to Study Cell Biology on the Nanoscale", Nanotechnology, 2002, pp. 285-289, vol. 13.
Dittami et al., "Electrically Evoking and Electrochemically Resovling Quantal Release on a Microchip", Lab on a Chip—Miniaturisation for Chemistry and Biology, 2010, pp. 30-35, vol. 10.
Elhamdani et al., "Quantal Size is Dependent on Stimulation Frequency and Calcium Entry in Calf Chromaffin Cells", Neuron, Sep. 13, 2001, pp. 819-830, vol. 31.
Fiaccabrino et al., "Array of Individually Addressable Microelectrodes", Sensors and Actuators: B. Chemical, 1994, pp. 675-677, vol. 19.
Fox et al., "Electroporation of Cells in Microfluidic Devices: A Review", Analytical and Bioanalytical Chemistry, 2006, pp. 474-485, vol. 385.
Fromherz et al., "Silicon-Neuron Junction: Capacitive Stimulation of an Individual Neuron on a Silicon Chip", Physical Review Letters, Aug. 21, 1995, pp. 1670-1673, vol. 75, No. 8.
Gao et al., "A Microfluidic Cell Trap Device for Automated Measurement of Quantal Catecholamine Release from Cells", Lab on a Chip—Miniaturisation for Chemistry and Biology, 2009, pp. 3442-3446, vol. 9.
Gao et al., "Magnetron Sputtered Diamond-Like Carbon Microelectrodes for On-Chip Measurement of Quantal Catecholamine Release from Cells", Biomedical Microdevices, 2008, pp. 623-629, vol. 10.
Hafez et al., "Electrochemical Imaging of Fusion Pore Openings by Electrochemical Detector Arrays", Proceedings of the National Academy of Sciences of the United States of America, 2005, pp. 13879-13884, vol. 102.
Hai et al., "Long-Term, Multisite, Parallel, In-Cell Recording and Stimulation by an Array of Extracellular Microelectrodes", Journal of Neurophysiology, Jul. 2010, pp. 559-568, vol. 104.
Hay et al., "Resolution of Regulated Secretion into Sequential MgATP-dependent and Calcium-dependent Stages Mediated by Distinct Cytosolic Proteins", The Journal of Cell Biology, Oct. 1992, pp. 139-151, vol. 119, No. 1.
Hochstetler et al., "Real-Time Amperometric Measurements of Zeptomole Quantities of Dopamine Released from Neurons", Analytical Chemistry, 2000, pp. 489-496, vol. 72.
Ino et al., "Addressable Electrode Array Device with IDA Electrodes for High-Throughput Detection", Lab on a Chip—Miniaturisation for Chemistry and Biology, 2011, pp. 385-388, vol. 11.
Lambie et al., "Experimentally Determining the IR Drop in Solution at Carbon Fiber Microelectrodes with Current Interruption and Application to Single-Cell Electroporation", National Institues of Health Public Access, 2008, pp. 1-21.
Liu et al., "Microwell Device for Targeting Single Cells to Electrochemical Microelectrodes for High-Throughput Amperometric Detection of Quantal Exocytosis", Analytical Chemistry, 2011, pp. 2445-2451, vol. 83, No. 7.
Long et al., "Noise at Microelectrodes and Microelectrode Arrays in Amperometry and Voltammetry", Analytical Chemistry, 1988, pp. 2309-2311, vol. 60, No. 20.
Martic et al., "Enzymatically Modified Peptide Surfaces: Towards General Electrochemical Sensor Platform for Protein Kinase Catalyzed Phosphorylations", Analyst, Jan. 7, 2011, pp. 107-112, vol. 136 Issue 1.
Matsue et al., "Electron-Transfer Reactions Associated with Host-Guest Complexation. Oxidation of Ferrocenecarboxylic Acid in the Presence of .beta.-Cyclodextrin", Journal of the American Chemical Society, 1985, pp. 3411-3417, vol. 107.
Neher et al., "Electrophysiological and Electrochemical Techniques for Studying Control Mechanisms of Secretion in Neuroendocrine Cells", Bioelectrochemistry and Bioenergetics, 1995, pp. 251-253, vol. 38.
Olofsson et al., "Single-Cell Electroporation", Current Opinion in Biotechnology, 2003, pp. 29-34, vol. 14.
Pei et al., "Individually Addressable Gel-Integrated Voltammetric Microelectrode Array for High-Resolution Measurement of Concentration Profiles at Interfaces", Analytical Chemistry, 2001, pp. 2273-2281, vol. 73.
Plattner et al., "Ultrastructural Organization of Bovine Chromaffin Cell Cortex-Analysis by Cryofixation and Morphometry of Aspects Pertinent to Exocytosis", The Journal of Cell Biology, Dec. 1997, pp. 1709-1717, vol. 139, No. 7.
Ryttsen et al., "Characterization of Single-Cell Electroporation by Using Patch-Clamp and Fluorescence Microscopy", Biophysical Journal, Oct. 2000, pp. 1993-2001, vol./No. 79(4).
Segura et al., "Automatic Analysis for Amperometrical Recordings of Exocytosis", Journal of Neuroscience Methods, 2000, pp. 151-156, vol. 103.
Sen et al., "Preferential Cell Attachment to Nitrogen-Dopes Diamond-Like Carbon (DLC:N) for the Measurement of Quantal Exocytosis", Biomaterials, 2009, pp. 1604-1612, vol. 30, No. 8.
Shin, "Nano- and Micro-Scale Studies of Exocytosis", A Dissertation presented to the Faculty of the Graduate School University of Missouri-Columbia, May 2007, pp. 1-119.

(56) References Cited

OTHER PUBLICATIONS

Spegel et al., "Fully Automated Microchip System for the Detection of Quantal Exocytosis from Single and Small Ensembles of Cells", Lab on a Chip—Miniaturisation for Chemistry and Biology, 2008, pp. 323-329, vol. 78.

Spegel et al., "On-Chip Determination of Dopamine Exocytosis Using Mercaptopropionic Acid Modified Microelectrodes", Electroanalysis, 2007, pp. 263-271, vol. 19. No. 2-3.

Sun et al., "On-Chip Amperometric Measurement of Quantal Catecholamine Release Using Transparent Indium Tin Oxide Electrodes", Analytical Chemistry, 2006, pp. 2521-2525, vol. 78.

Vasanelli et al., "Space and time-resolved gene expression experiments on cultured mammalian cells by a single-cell electroporation microarray", New Biotechnology, Jun. 2008, vol. 25, No. 1.

Wang et al., "Single-Cell Electroporation", Analytical and Bioanalytical Chemistry, 2010, pp. 3235-3248, vol. 397.

Wegener et al., "Recovery of Adherent Cells after In Situ Electroporation Monitored Electrically", BioTechniques, Aug. 2002, pp. 348-357, vol. 33, No. 2.

Wightman et al., "Temporally Resolved Catecholamine Spikes Correspond to Single Vesicle Release from Individual Chromaffin Cells", Proceedings of the National Academy of Sciences of the United States of America, 1991, pp. 10754-10758, vol. 88.

Wilson et al., "Multiplex Measurement of Seven Tumor Markers Using an Electrochemical Protein Chip", Analytical Chemistry, 2006, pp. 6476-6483, vol. 78.

Yang et al., "Phosphomimetic Mutation of Ser-187 of SNAP-25 Increases Both Syntaxin Binding and Highly Ca2+-Sensitive Exocytosis", Journal of General Physiology, 2007, pp. 233-244, vol. 129, No. 3.

Yao et al., "A high-throughput electrochemical microelectrode array for amperometric measurement", Abstract, World Congress on Bioengineering, WACBE World Association for Chinese Biomedical Engineers, Aug. 18-21, 2011, www.wacbe.org.

Yao et al., "A Novel Multiplexing Approach for Individually Addressable Electrode Arrays with Reduced External Connections", Abstract, Biomedical Engineering Society, Oct. 12-15, 2011, Hartford, CT, www.bmes.org.

Yao et al., "A Low Noise Electrochemical Microelectrode Array for Measurement of Cell Secretion", Poster presented at the 5th World Congress on Bioengineering 2011, Tainan, Taiwan, Dalton Cardiovascular Research Center, Department of Biological Engineering, Department of Pharmacology and Physiology, University of Missouri, Columbia, 1 Page.

Yao et al., "Quantification of Noise Sources for Amperometric Measurement of Quantal Exocytosis Using Microelectrodes", Analyst, 2012, pp. 2674-2681, vol. 137.

Yao et al.,"A Multiplexed Electrochemical Electrode Array for High Throughput Measurements of Quantal Exocytosis", Biophysical Journal, Feb. 2011, pp. 607a, vol. 100, Issue 3, Supplement 1.

Zeck et al., "Noninvasive Neuroelectronic Interfacing With Synaptically Connected Snail Neurons Immobilized on a Semiconductor Chip", Proceedings of the National Academy of Sciences, Aug. 28, 2001, pp. 10457-10462, vol. 98, No. 18.

Zor et al., "Real-Time Monitoring of Cellular Dynamics Using a Microfluidic Cell Culture System with Integrated Electrode Array and Potentiostat", 15th International Conference on Miniatured Systems for Chemistry and Life Sciences, Oct. 2-6, 2011, Seattle, Washington, USA, pp. 1532-1535.

\* cited by examiner

| $V_S$ | $V_{f1}$ | $V_{WE1}$ | WE1 Status | $V_{f2}$ | $V_{WE2}$ | WE2 Status |
|---|---|---|---|---|---|---|
| 0.6V | GND | 0.6V | Enabled | 0.6V | 0 | Disabled |
| 0.6V | 0.6V | 0 | Disabled | GND | 0.6V | Enabled |

FIG. 3

| $V_S$ | $V_{f1}$ | $V_{WE2}$ | WE1 Status | $V_{f2}$ | $V_{WE2}$ | WE2 Status |
|---|---|---|---|---|---|---|
| -0.2V | GND | -0.2V | Enabled | -0.8V | 0.6V | Disabled |
| -0.2V | -0.8V | 0.6V | Disabled | GND | -0.2V | Enabled |

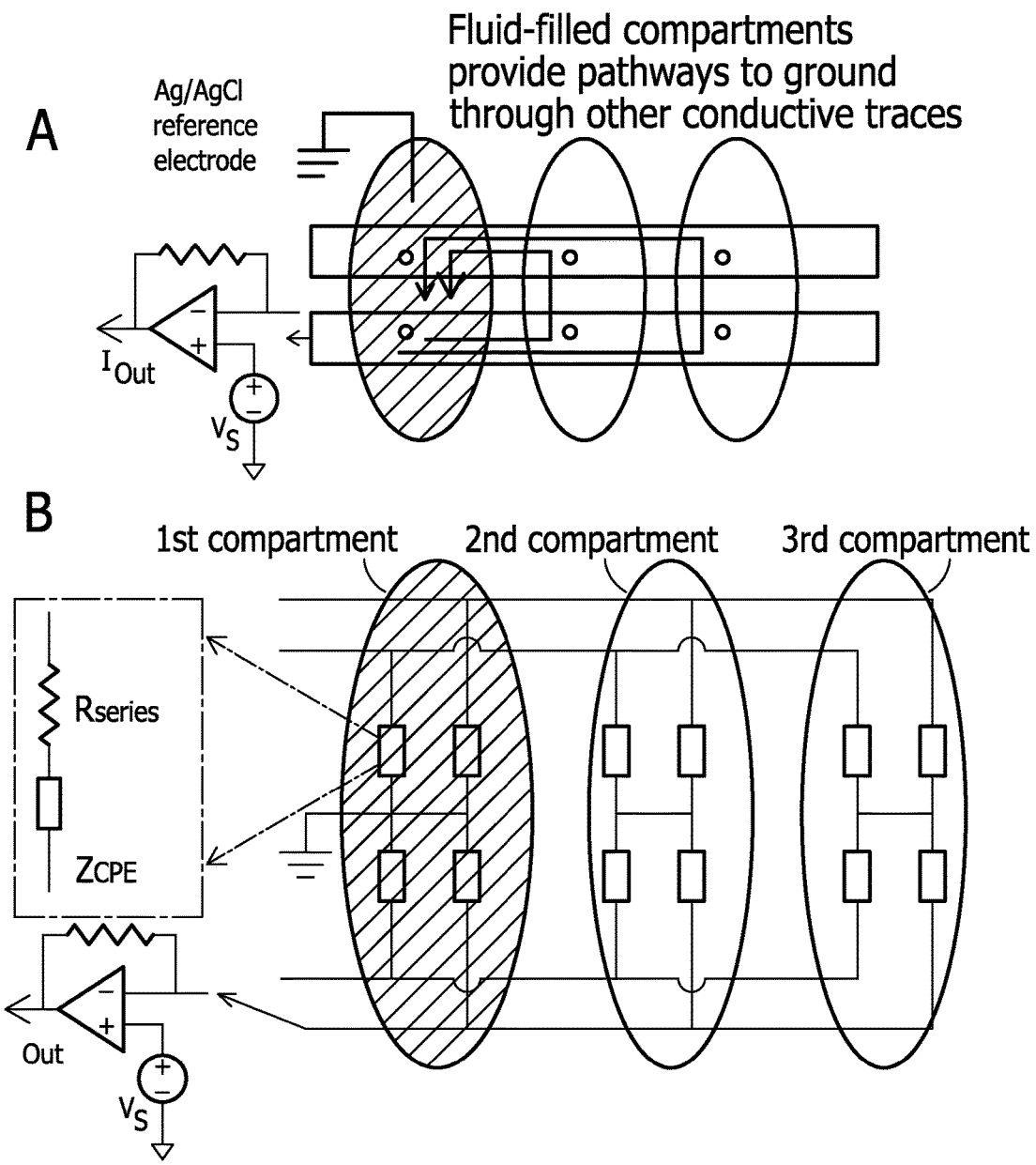
FIG. 10 A,B

ADDRESSABLE ELECTRODE ARRAYS IN MULTIPLE FLUIDIC COMPARTMENTS AND USES THEREOF

CROSS-REFERENCE TO RELATED APPLICATIONS

This non-provisional U.S. patent application claims the benefit of U.S. Provisional Patent Application No. 61/713,408, filed Oct. 12, 2012, and incorporated herein by reference in its entirety.

STATEMENT REGARDING FEDERALLY SPONSORED RESEARCH OR DEVELOPMENT

This invention was made with government support under Grant No. NIH R01 NS048826 and R01 MH095046 awarded by the National Institute for Health of the United States of America. The government has certain rights in the invention.

BACKGROUND

The lab-on-a-chip field is driven by the ability of photolithography to pattern materials at a very high density in a rapid and economical manner. Among many other applications, photolithography has enabled development of electrochemical electrode arrays that can be used, for example, for resolution of spatial gradients of analytes (Pei et al. 2001), measurement of multiple analytes in a sample (Wilson and Nie 2006), or high throughput measurement of transmitter released from individual cells (Amatore et al. 2007; Amatore et al. 2006; Barizuddin et al. 2010; Berberian et al. 2009; Chen et al. 2003; Chen et al. 2007; Dias et al. 2002; Dittami and Rabbitt 2010; Gao et al. 2009; Gao et al. 2008; Hafez et al. 2005; Liu et al. 2011; Sen et al. 2009; Spégel et al. 2007; Spégel et al. 2008; Sun and Gillis 2006). One limitation of electrochemical electrode arrays is that it is often inconvenient to make connections between external amplifiers and hundreds, or potentially even thousands, of electrodes on the device. This is particularly the case if the array device needs to be replaced regularly while performing assays in a high throughput manner.

A similar connectivity issue occurs in other high-density microdevices such as charge-coupled-device cameras or digital memory chips and is resolved using "time-division multiplexing" whereby data originating from multiple elements are sequentially read out using a relatively small number of data lines. In this way the number of external connections can be over a million-fold fewer than the number of elements to be read. Central to this approach are methods to address each data element. For example, if the elements are arranged in a rectangular array, each element can be read using an address consisting of the row and column number of the element.

Time-division multiplexing of electrochemical electrode arrays has been implemented with off-chip multiplexers (Pei, et al. 2001). This reduces the number of external potentiostats required, but the number of connections required to the array is still equal to the number of working electrodes. Thus most of the chip "real estate" is used for making connections rather than serving as sensing elements. True on-chip addressing of electrochemical electrodes was carried out by Fiaccabrino et al., using an NMOS analog multiplexer fabricated on a silicon wafer (Fiaccabrino et al. 1994). However, this application is limited to cases where the electrode array is directly patterned on silicon. Glass is often the preferred substrate for electrochemical electrode arrays because it is inexpensive, has a high shunt resistance and low stray capacitance, and is transparent to allow combination of electrochemical and optical measurements.

Ino et al. recently reported an addressable electrochemical electrode array on a glass substrate where row and column electrodes are patterned in an interdigitated array to allow redox cycling to be activated at individually addressed sensing elements (Ino et al. 2011). This device appears to be limited to applications using redox cycling. In addition, since the array is placed in a single fluid compartment, the effective area of the generator and collector electrodes is larger, and thus the recordings are noisier than if an individual set of microelectrodes is used.

SUMMARY

Whereas patterning hundreds or thousands of electrochemical electrodes on lab-on-a-chip devices is straightforward and cost-effective using photolithography, easily making connections between hundreds of electrodes and external amplifiers remains a bottleneck. The inventors disclose an electrode addressing approach using multiple fluid compartments that can potentially reduce the number of external connections by ~100-fold while maintaining an amperometric noise level comparable to that of an individual electrode. In certain embodiments, the apparati and associated methods provided herein can yield low noise measurements of biological processes and/or electrochemical reactions by selectively enabling an electrode in one fluid-filled compartment and taking a measurement from that enabled compartment while the other fluid filled compartments are disabled. In certain embodiments, the process of selectively enabling and measuring an electrode in a single compartment while disabling the other compartments is sequentially repeated across an addressable array of compartments to provide for a measurement in each compartment of the array.

The inventors believe that the throughput for measurements via the inventive electrode array can be greatly improved while still benefiting from low noise measurements. Because working electrodes can be selectively enabled and disabled, even when the fluid compartments in which they are located contain a fluid, a practitioner is permitted to fill several (or all) of the fluid compartments prior to a measuring sequence rather than forcing the practitioner to fill and empty fluid compartments one at time for each measurement in order to enjoy low noise measurements.

In an alternative embodiment, low noise measurements of biological processes and/or electrochemical reactions are provided by filling only one compartment of the array with solution at a time, measuring the signal in that compartment, removing fluid and optionally washing the compartment, and repeating that process on successive compartments. At least one other advantage of apparati provided herein is that the fraction of the microchip area that needs to be dedicated to making external connections is reduced, thereby reducing the cost per working electrode.

Methods for measuring a signal, comprising: enabling a first electrode of an electrode array, a plurality of the electrodes of the electrode array being in contact with a fluid, the fluid being contained by a plurality of compartments; while the first electrode is enabled, disabling a plurality of electrodes of the electrode array other than the first electrode, the other electrodes also being in contact with the fluid; and measuring a signal produced by the enabled first electrode while the other electrodes are disabled are provided. In certain embodiments, each of at least a plurality of the compartments has an electrode of the electrode array located therein, wherein the disabling step comprises: while the first electrode is enabled, disabling a plurality of the electrodes of the electrode array that are located in a fluid-containing compartment other than the fluid-containing compartment in which the first electrode is located. In certain embodiments of the aforementioned methods, the disabling step further comprises: while the first electrode is enabled, disabling all of the electrodes of the electrode array that are located in a fluid-containing compartment other than the fluid-containing compartment in which the first electrode is located. Certain embodiments of the aforementioned methods can further comprise repeating the enabling step, the disabling step, and the measuring step while using a different electrode of the electrode array as the first electrode. In certain embodiments of the aforementioned methods, the first electrode is at a first voltage potential, and wherein the enabling step comprises connecting the fluid-containing compartment in which the first electrode is located to a second voltage potential via a reference electrode, a relationship between the first voltage potential and the second voltage potential causing a current to flow through the fluid via the first electrode. In certain embodiments of the aforementioned method, the second voltage potential is ground voltage. In certain embodiments of the aforementioned methods, the disabling step comprises: while the first electrode is enabled, connecting each fluid-containing compartment in which the first electrode is not located to a third voltage potential via a reference electrode, a relationship between the first voltage potential and third voltage potential preventing an appreciable current from flowing through the fluid via each disabled electrode. In certain embodiments of the aforementioned methods, the third voltage potential is substantially equal to the first voltage potential. In certain embodiments of the aforementioned method, the third voltage potential is sufficient to prevent a reaction by the fluid in each fluid-containing compartment in which the first electrode is not located. In certain embodiments of the aforementioned methods, the third voltage potential is sufficient to cause a reaction by the fluid in each fluid-containing compartment in which the first electrode is not located. In certain embodiments, the aforementioned methods can comprise varying the first voltage potential over time. In certain embodiments of the aforementioned methods, the fluid comprises a plurality of different fluids such that at least two of the compartments contain different fluids. In certain embodiments of the aforementioned methods, the electrodes of the electrode array comprise electrochemical electrodes. In certain embodiments, the aforementioned methods can comprise:

filling a plurality of the compartments with the fluid; and performing the enabling step, the disabling step, and the measuring step while the compartments are filled with the fluid. In certain embodiments of the aforementioned method, the filling step comprises filling all of the compartments with the fluid prior to the performing step. In certain embodiments of the aforementioned methods, the filling step comprises simultaneously filling all of the compartments with the fluid prior to the performing step. In certain embodiments of the aforementioned methods, the fluid comprises a plurality of different fluids, and wherein the filling step comprises filling at least one of the compartments with a first fluid and filling at least one of another of the compartments with a second fluid. In certain embodiments of the aforementioned methods, the measuring step comprises at least one of an amperometric, cyclic voltammetric, or chronoamperometric measurement. In certain embodiments of the aforementioned methods, the fluid comprises biological cells or biological molecules. In certain embodiments of the aforementioned methods, the measuring step comprises measuring a signal produced by at least one of exocytosis, non-exocytotic release of a substance, ion-channel activity, ion-pump activity, enzyme activity, receptor activity, protease activity, kinase activity, uptake or transport of a substance into a cell, or an action potential. In certain embodiments of the aforementioned methods, one or more of said compartments are filled with fluid containing an electrochemically active analyte. In certain embodiments of the aforementioned methods, the disabling step comprises disabling all of the electrodes of the electrode array other than the first electrode. In certain embodiments of the aforementioned methods, the first electrode comprises only one electrode of the electrode array. In certain embodiments of the aforementioned methods, at least a plurality of the compartments further contain a plurality of the electrodes of the electrode array. In certain embodiments, the aforementioned methods can further comprise repeating the enabling step, the disabling applying step, and the measuring step while using a different electrode of the electrode array as the first electrode until all of the electrodes have been used as the first electrode.

Also provided are apparati for measuring a signal, comprising: a plurality of working electrodes, the plurality of working electrodes comprising a first working electrode and a second working electrode; a conductive path between the first and second working electrodes; a plurality of compartments for containing a fluid, the compartments comprising a first compartment in which the first working electrode is located and a second compartment in which the second working electrode is located; a plurality of reference electrodes, the plurality of reference electrodes comprising a first reference electrode located in the first compartment and a second reference electrode located in the second compartment, the first reference electrode not being in direct contact with the first working electrode, the second reference electrode not being in direct contact with the second working electrode; and circuitry configured to selectively enable and disable the first and second working electrodes based on (1) a first controllable voltage potential relationship between the first reference electrode and the first working electrode and (2) a second controllable voltage potential relationship between the second reference electrode and the second working electrode. In certain embodiments, the circuitry comprises a plurality of switches, the switches configured to switch the reference electrodes between a plurality of voltage potentials in response to a control signal. In certain embodiments, the plurality of switches comprises a first switch and a second switch, the first switch configured to switch the first reference electrode between a ground voltage and a first voltage potential in response to a control signal, the second switch configured to switch the second reference electrode between a ground voltage and a second voltage potential in response to a control signal. In certain embodiments, the first and second voltage potentials are the same voltage amount. In certain embodiments, the circuitry further comprises a controller, the controller configured to provide a control signal to the switches, the control signal configured to vary over time, the control signal comprising a first control signal state and a second control signal state, the first control signal state configured to enable the first working electrode while disabling the second working electrode, the second control signal state configured to disable the first working electrode while enabling the second working electrode. In certain embodiments, the controller is configured to vary the control signal over time in accordance with a sequence that causes each working electrode to become enabled while a plurality of the working electrodes located in compartments other than the enabled working electrode are disabled. In certain embodiments of any of the aforementioned apparati, the circuitry comprises measuring circuitry, the measuring circuitry configured to connect the enabled working electrode to a voltage potential to measure a signal via the enabled working electrode. In certain embodiments, the circuitry is further configured to vary the voltage potential to which the enabled working electrode is connected over time. In certain embodiments of any of the aforementioned apparati, the first working electrode, the second working electrode, and the conductive path are formed from a conductor having an insulated covering, the insulating covering having a plurality of openings, the openings defining the first and second working electrodes. In certain embodiments, any of the aforementioned apparati can comprise a plurality of N of conductors and a plurality M of the compartments, a plurality M of the reference electrodes, and a plurality N×M of the working electrodes, each working electrode being located on a conductor, each compartment having N working electrodes located therein, wherein one of the conductors comprises the conductive path, wherein N and M are each greater than 2. In certain embodiments, any of the aforementioned apparati can further comprise a fluid contained within the first and second compartments, the fluid in the first compartment causing a fluid connection between the first working electrode and the first reference electrode, the fluid in the second compartment causing a fluid connection between the second working electrode and the second reference electrode. In certain embodiments, the apparati can further comprise a plurality of counter electrodes, the plurality of counter electrodes comprising a first counter electrode and a second counter electrode, the first counter electrode being located in the first compartment, the second counter electrode being located in the second compartment.

Methods for measuring a signal via an apparatus, the apparatus comprising (1) a plurality of conductors, (2) a plurality of electrodes arranged as an electrode array, and (3) a plurality of compartments for containing a fluid, and wherein each compartment contains at least one of the electrodes, the method comprising: filling a plurality of the compartments with a fluid; enabling a selected electrode of the electrode array; while the selected electrode is enabled and while the compartments are filled with the fluid, electrically blocking a current path through the fluid compartments that do not contain the enabled electrode; measuring a signal from the enabled electrode while the current path is electrically blocked are provided. In certain embodiments, the methods can further comprise repeating the enabling, electrically blocking, and measuring steps for different selected electrodes of the electrode array.

Methods for measuring a signal via an apparatus, the apparatus comprising (1) a plurality of conductors, (2) a plurality of electrodes arranged as an electrode array, and (3) a plurality of compartments for containing a fluid, wherein each conductor contacts a plurality of the electrodes, and wherein each compartment contains a plurality of the electrodes, the method comprising: filling a plurality of the compartments with a fluid; within a fluid compartment containing a selected electrode of the electrode array, disabling a reaction by the fluid; while the fluid reaction is disabled within the fluid compartment containing the selected electrode, enabling a fluid reaction in the fluid compartments that contain a plurality of the electrodes other than the selected electrode; measuring a signal from the selected electrode while (1) the fluid reaction within the fluid compartment containing the selected electrode is disabled and (2) the fluid reaction within the fluid compartments containing the electrodes other than the selected electrode is enabled are provided. In certain embodiments, the methods can further comprise repeating the enabling, electrically blocking, and measuring steps for different selected electrodes of the electrode array.

An apparatus, method, system and/or computer-readable storage medium exhibiting any combination of the features described herein is also provided.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention.

FIG. 3 illustrates a table of appropriate Vs, Vf1, Vwe1, Vf2, and $V_{WE2}$ values, as well as the corresponding WE1 and WE2 statuses, for measuring an exemplary epinephrine analyte with exemplary devices shown in FIGS. 1, 2, 5, and 6.

FIG. 4 illustrates a table of applicable values for appropriate Vs, Vf1, Vwe1, Vf2, $V_{WE2}$ values, as well as the corresponding WE1 and WE2 statuses, for measuring an exemplary ferricyanide analyte with exemplary devices shown in FIGS. 1, 2, 5, and 6.

FIG. 10A, B illustrates that "floating" fluid-filled compartments provide a pathway to ground through other electrochemical electrodes in the array. (A) Schematic illustration of multiple pathways to ground. (B) Equivalent circuit representation.

DETAILED DESCRIPTION

Definitions

As used herein, the phrase 'electrochemically active analyte" refers to any compound that can undergo an oxidation or reduction reaction.

As used herein, the term "filled", when used in reference to a fluid containing compartment, refers to an amount of fluid sufficient to provide for enabling and disabling an electrode in the compartment and for measuring a signal in the compartment. A compartment may thus be filled when it is either all or a portion of the compartment contains the fluid.

As used herein, the term "filling", when used in reference to adding fluid to a compartment, encompasses the sequential or simultaneous addition of one or more fluids to the compartment. Filling of a compartment can thus comprise any of the addition of a single fluid in a single step or multiple step(s), the addition of distinct fluids in a single or multiple step(s), and any combination thereof.

Further Description

Methods of measuring signals and related apparati comprising arrays of compartments containing electrodes that can be selectively enabled or disabled are provided herein. Such selective enablement of an electrode in the array where a measurement is made, accompanied by the selective disablement of other electrodes where a measurement is not made, can allow measurements to be made from multiple samples using a reduced number of conductors on the device.

Figure 1:
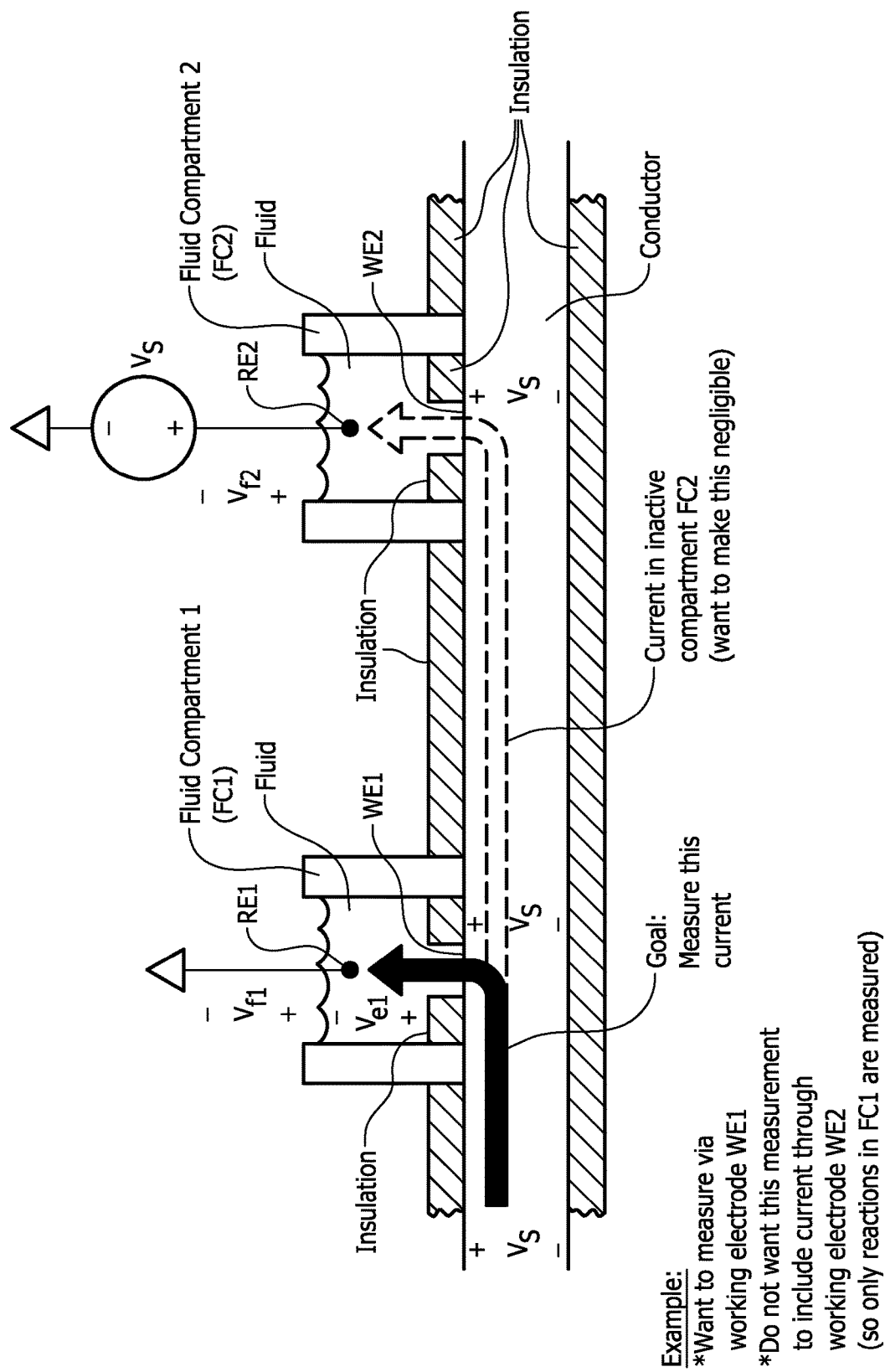
FIG. 1 depicts a general cross-sectional view of an array portion that illustrates a goal in connection with enabling and disabling electrodes of the electrode array.

Exemplary apparati comprising arrays of compartments containing electrodes that can be selectively enabled or disabled are described hereinafter FIG. 1 depicts a general cross-sectional view of an array portion that illustrates a goal in connection with enabling and disabling electrodes of the electrode array. The array can comprise a conductor. Working electrodes, WE1 and WE2, can contact the conductor. The working electrodes can either be attached to the conductor or formed from the conductor via openings in insulation around the conductor. The working electrodes are also located in compartments that are configured to contain a fluid. For example, WE1 is located in Fluid Compartment 1 (FC1) and WE2 is located in Fluid Compartment 2 (FC2). FC1 and FC2 contain a fluid in this example.

Also shown in FIG. 1 is a reference electrode RE1 located in FC1 and a reference electrode RE2 located in FC2. RE1 does not directly contact WE1, but there is a fluidic connection between WE1 and RE1. Likewise, RE2 does not directly contact WE2, but there is a fluidic connection between WE2 and RE2. The reference electrodes can be wires inserted into the fluid compartment.

In the example of FIG. 1, it is desired to measure a signal corresponding to a characteristic of the fluid contained by F1 via WE1. To do so, FIG. 1 shows WE1 being enabled while WE2 is disabled.

If the conductor is driven to voltage potential Vs, and RE1 is connected to ground in this example, a current will flow through the conductor to ground via WE1, the fluid, and RE1 (see the current identified in FIG. 1 by heavy lines). As such, WE1 can be described as being enabled. The voltage drop across WE1, labeled as Ve1 in FIG. 1, can be characterized as Vs-0, or Vs. Because this current can be indicative of a characteristic of the fluid in FC1, it is desired to measure this current with accuracy. However, if an alternative path for current to ground exists through FC2 (see the current shown by broken lines in FIG. 1), then this alternative current path can introduce interference into the measured signal. That is, it is desired that the current measured from the conductor reflect the state of FC1 and not also the state of FC2. However, if a current flows through FC2, the measured current would also reflect the state of FC2, which would be deemed interference with respect to the desired measurement.

To solve this problem, the inventors disclose that WE2 can be disabled to electrically block the current through FC2. In the example of FIG. 1, RE2 can be connected to the same voltage potential that WE2 has been driven to. By connecting RE2 to Vs, no voltage drop occurs across WE2 because WE2 also resides at Vs (i.e., the voltage drop across WE2, labeled as Ve2 in FIG. 1, is Vs-Vs or 0). As such, WE2 can be described as being disabled. While WE2 is disabled, the current through FC2 not appreciable (i.e. negligible at most—contributing to no more than 5% of the current measured for WE1), and accurate signal measurements via enabled WE1 can be performed.

Figure 2:
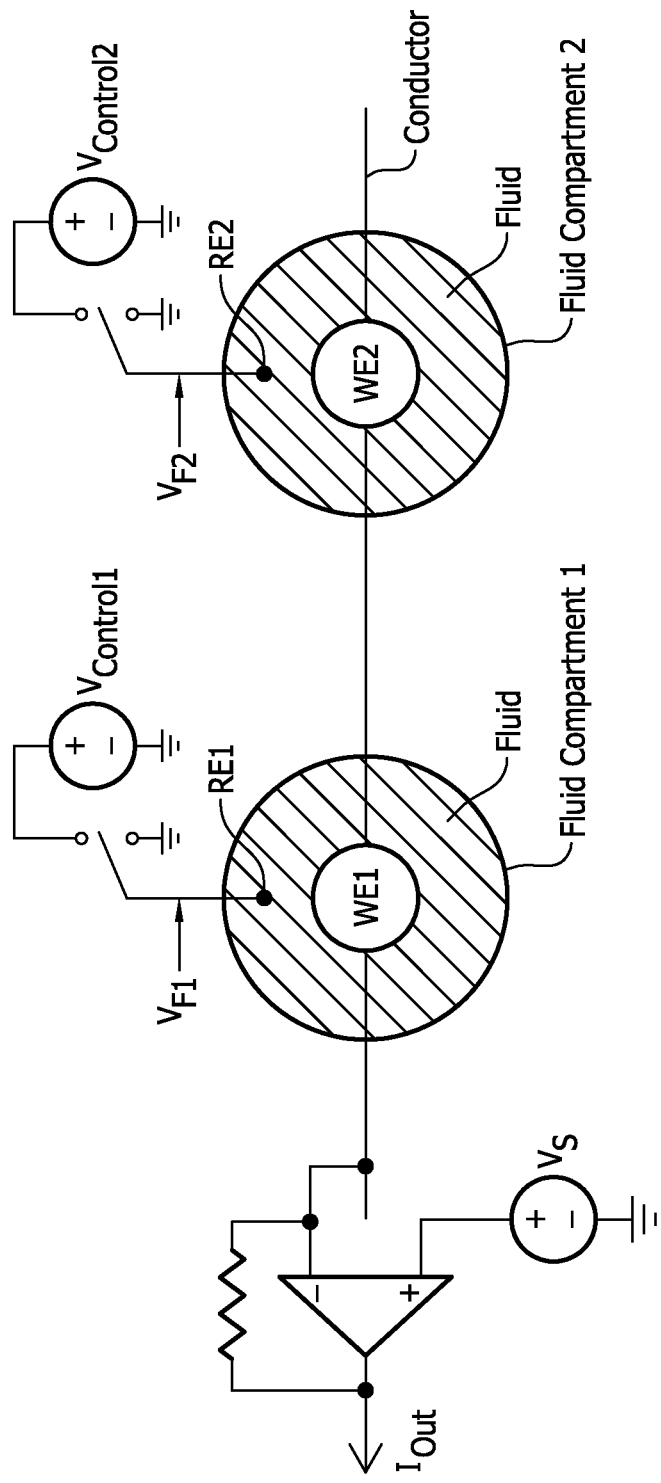
FIG. 2 illustrates an embodiment employing switches to controllably enable/disable each working electrode.

To permit active switching of which working electrode is enabled and which is disabled, FIG. 2 illustrates an embodiment employing switches to controllably enable/disable each working electrode. As shown in FIG. 2, RE1 is connected via a switch to either ground or Vcontrol1 (where Vcontrol1 can also be referred to as Vc1). RE2 is connected via a switch to either ground or Vcontrol2 (where Vcontrol2 can also be referred to as Vc2). Thus, depending on the state of the switch for RE1, the voltage potential Vf1 can be either ground voltage or Vcontrol1. Similarly, depending on the state of the switch for RE2, the voltage potential Vf2 can be either ground voltage or Vcontrol1. Furthermore, a current measuring circuit is connected to the conductor, where this current measuring circuit is configured to drive the conductor, and thus WE1 and WE2, to the voltage potential Vs. In the example of FIG. 2, the classic op amp/resistor circuit is used to measure the current flowing through the conductor.

Furthermore, it should be understood that a controlling factor in the selective enablement/disablement of the working electrodes is the voltage potential relationship between Vs and Vf. Thus, while the examples of FIGS. 1-4 involve holding Vs steady while adjusting Vf, it should be understood that this voltage potential relationship can be controlled not only by adjusting Vf but also by adjusting Vs. As such, a practitioner may choose to hold Vf steady while controllably adjusting Vs to achieve a desired enablement and disablement of the working electrodes. Still further, a practitioner may choose to controllably adjust both Vs and Vf to achieve a desired enablement and disablement of the working electrodes. FIG. 6 shows an exemplary measuring circuit that is configured to support an adjustable Vs. A controller can provide a control signal to a multiplexer to select which of a plurality of voltage amounts will be passed to the op amp. A DAC with an input register can be used to define an adjustable value for Vs. As with the control circuitry of FIG. 5, it should be understood that other arrangements for controlling the value of Vs can be implemented.

Thus, continuing from the discussion above, in a case where the voltage applied, relative to earth ground, is Vs for each working electrode, and the voltage applied to a particular fluid compartment is Vf relative to earth ground, the voltage difference across each electrode is given by Ve=Vs−Vf. In certain embodiments, enabling or disabling each electrodes in each fluid filled compartment of a multi-compartmented array can be accomplished by setting the value of Vf in each compartment. In an enabled compartment where a measurement is to be made, Vf can be adjusted in that compartment to a value of zero (0) such that Ve=Vs while in disabled compartments on the same array where a measurement is not to be made, Vf can be adjusted in that compartment to a value such that Vs=Vf and Ve=0. But again, a practitioner may choose to enable or disable each electrodes in each fluid filled compartment of a multi-compartmented array by adjusting the value of Vs in each compartment instead.

The exact voltage values used for Vs, Vc1, and Vc2 that are used by a practitioner to govern the enablement/disablement of WE1 and WE2 can be variable depending on the analytes and/or fluids that are present in the fluid compartments.

In an exemplary and non-limiting method and apparatus where the analyte is a weak reducing agent (i.e. is not readily oxidized at a working electrode with a Ve value=0), electrodes in a given fluid compartment are disabled by setting Vf=Vs so that Ve=0 for any value of Vs. In contrast, a fluid compartment where a measurement of that analyte is to be made would be enabled by setting Vf=0, so that Ve=Vs. Oxidation and measurement of that analyte in an enabled fluid compartment could then be carried out by setting Vs in that compartment to a sufficiently positive potential that results in oxidation of the analyte. Weak reducing agents that can be measured in this manner include, but are not limited to, catecholamines such as epinephrine. For the illustrative and non-limiting case of an epinephrine analyte, a Ve=0.6V is sufficient to provide for oxidation. Appropriate values of Ve at an enabled electrode for other analytes that comprise reducing agents can either be obtained from standard tables that provide redox potentials for the analyte under standard conditions of temperature, pH, ionic strength, and the like, and/or by empirical testing using positive control analytes under desired conditions of temperature, pH, ionic strength, and the like. Appropriate Vs, Vf1, Vwe1, Vf2, and $V_{WE2}$ values (including corresponding WE1 and WE2 statuses) for measuring an exemplary epinephrine analyte with the devices shown in FIG. 1 and FIG. 2 are provided in FIG. 3.

In an exemplary and non-limiting method and apparatus where the analyte is an oxidizing agent, reduction of the analyte at an electrode in an enabled compartment is measured. For disabled compartments, a positive Ve electrode potential is maintained to lead to a negligibly small reduction current in those compartments. In contrast, fluid compartments would be enabled by setting Vf=0, so that Ve=Vs where Vs to a sufficiently negative (reducing) potential. Appropriate values of Ve at an enabled electrode for other analytes that comprise oxidizing agents can either be obtained from standard tables that provide redox potentials for the analyte under standard conditions of temperature, pH, ionic strength, and the like, and/or by empirical testing using positive control analytes under desired conditions of temperature, pH, ionic strength, and the like. Oxidizing agents that can be measured in this manner include, but are not limited to, ferricyanide ($Fe(CN)_6^{3-}$). In an exemplary and non-limiting case, where ferricyanide is the analyte, the reduction of ferricyanide ($Fe(CN)_6^{3-}$) to ferrocyanide ($Fe(CN)_6^{4-}$) can be measured. In this illustrative case, a positive electrode potential (e.g., Ve=0.6V) is maintained to lead to a negligibly small reduction current in disabled compartments. In this example, all the electrodes in a given fluid compartment are disabled by setting Vf=Vs−0.6V so that Ve=+0.6V for any value of Vs. In contrast, fluid compartments would be enabled by setting Vf=0, so that Ve=Vs. Reduction of ferricyanide in enabled fluid compartments could then be carried out by setting Vs to a sufficiently negative (reducing) potential, e.g., Vs=−0.2V. Appropriate Vs, Vf1, Vwe1, Vf1, and $V_{WE2}$ values (including corresponding WE1 and WE2 statuses) for measuring an exemplary ferricyanide analyte with the devices shown in FIG. 1 and FIG. 2 are provided in FIG. 4.

In certain embodiments, the voltage across each working electrode of the apparatus is set by imposing a voltage at the reference electrode in each fluid compartment, described herein as "Vf". The "non-working" reference electrode that sets the fluid potential can be fabricated from a material that makes it relatively "non-polarizable". "Non-polarizable' materials include, but are not limited to, Ag/AgCl. In contrast, the working electrochemical electrode can be fabricated from a material that does not readily pass current in the absence of electrochemical reactions. In certain embodiments, the working electrochemical electrode materials include, but are not limited to, gold (Au), carbon, diamond-like carbon, platinum (Pt), nickel (Ni), palladium, and mercury. Therefore the voltage drop Ve occurs near the surface of the working electrode.

In certain embodiments of the methods and apparati provided herein, a nonpolarizing reference electrode is inserted in each fluid compartment. Such a reference electrode could comprise a Ag/AgCl wire. Each of these reference electrodes is connected to either an enabling or disabling voltage using manual switches, relays, solid-state multiplexer, or any other device that provides for selective application of a desired voltage to that electrode. In certain embodiments of the methods and apparati provided herein, a nonpolarizing reference electrode is directly fabricated on the electrode array that contains the working electrodes. There is only one reference electrode per fluid compartment. These reference electrodes are then connected to enabling or disabling voltages using switches, relays, multiplexers, or any other device that provides for selective application of a desired voltage to that electrode.

In certain other embodiments, a practitioner may choose to also position a counter electrode in a fluid compartment. Such an arrangement might be useful to minimize voltage drops in the fluid compartment and the reference electrode where relatively large currents are being measured. The counter electrode would be effectively paired with the working electrode sharing the same fluid compartment such that the bulk of current flowing within the fluid compartment will flow between the enabled working electrode and the counter electrode. In such an arrangement, the reference electrode would not pass any appreciable current, but would set the voltage for the fluid compartment.

Figure 5:
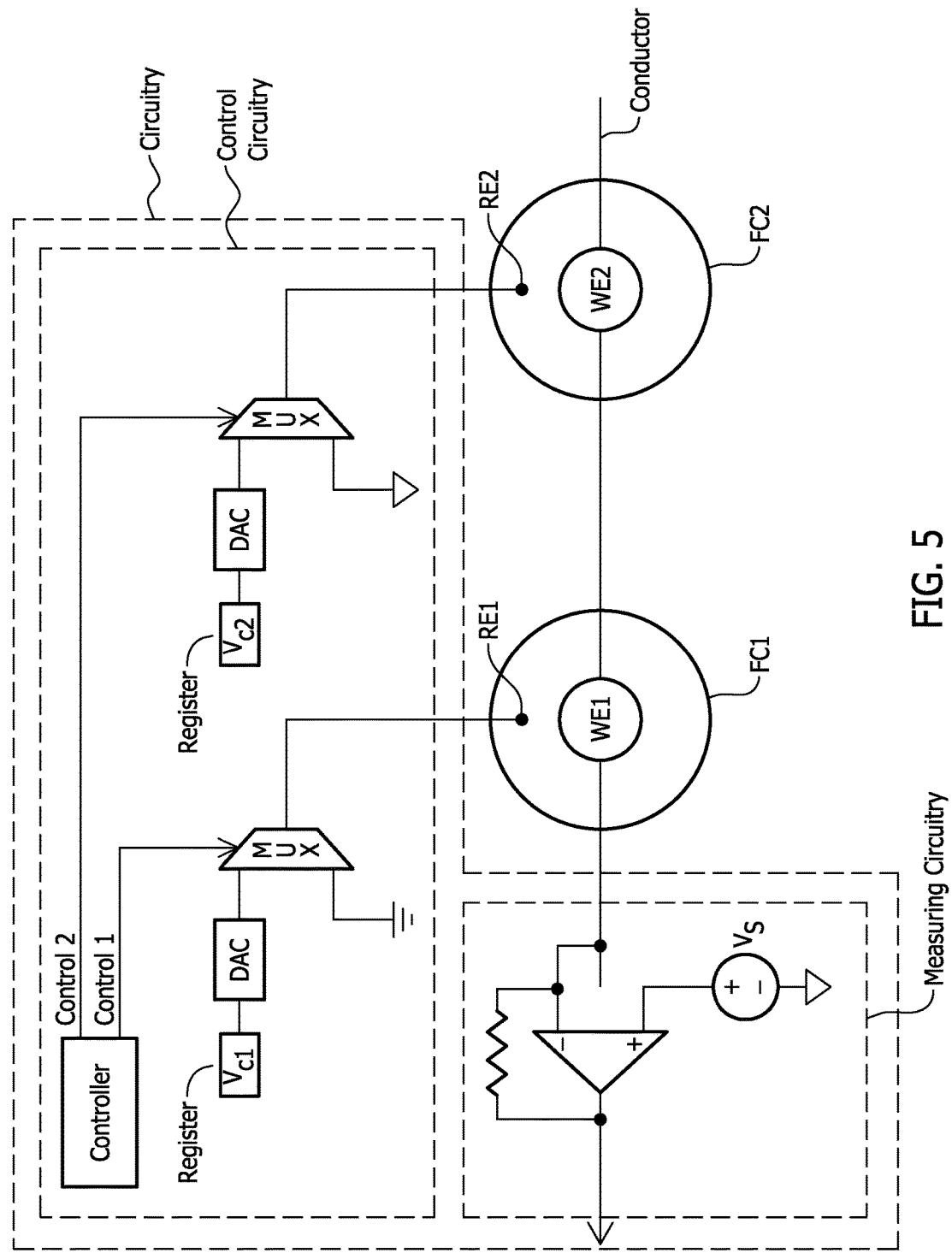
FIG. 5 shows an example of how circuitry can be used to selectively enable and disable the working electrodes.
Figure 6:
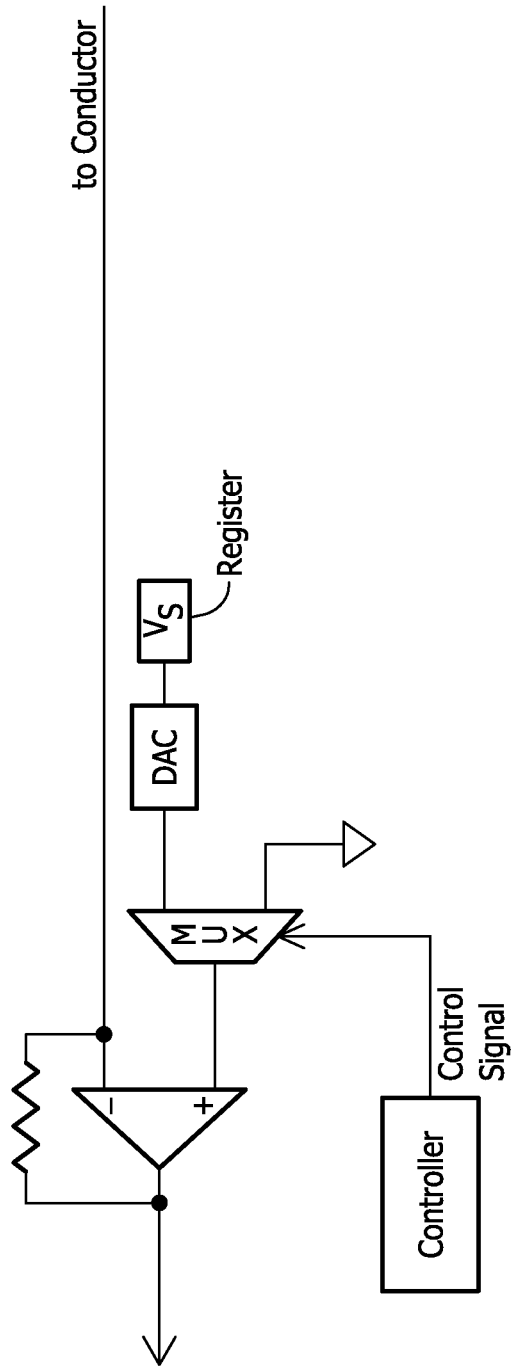
FIG. 6 shows an exemplary measuring circuit that is configured to support an adjustable Vs.

FIG. 5 shows an example of how circuitry can be used to selectively enable and disable the working electrodes. FIG. 5 shows circuitry that includes control circuitry and measuring circuitry. The measuring circuitry can be the op amp/resister/Vs arrangement shown in FIG. 2. The control circuitry for selectively driving the fluid compartments to a desired voltage to govern enablement/disablement can be implemented in any of a number of ways. For example, as shown in FIG. 5, a controller can generate a control signal including control signals Control1 and Control 2. Control1 can be applied to a first multiplexer to select whether a value corresponding to ground voltage or a value corresponding to Vc1 (via a digital-to-analog converter (DAC)) gets passed by the first multiplexer. Thus, the state of Control1 will operate to drive RE1 to the either ground voltage or Vc1. Similarly, Control 2 can be applied to a second multiplexer to select whether a value corresponding to ground voltage or a value corresponding to Vc2 gets passed to RE2. Furthermore, the controller can load the registers shown in FIG. 5 with the values to be used as Ve1 and Vc2. Thus, the Ve1 and Vc2 values can also be adjusted as desired by a practitioner.

A variety of devices that provide for selective application of a desired voltage to an electrode can be used in the methods and apparati provided herein. In certain embodiments, a circuit could use manually operated analog switches to set the voltage of electrodes in a fluid compartment to either an enabling or disabling value. In other embodiments, a circuit could use switches that are controlled by analog voltages or currents (e.g., relays) to apply voltages which enable or disable fluid compartments. In other embodiments, a circuit could use switches that are controlled by digital signals (e.g., multiplexers) to apply voltages which enable or disable fluid compartments. In other embodiments, digital signals that control the multiplexers can originate from a digital interface and allow automated sequential recordings from a series of fluid compartments. This automation can be realized in hardware using timing circuitry or can be realized in software following a sequential set of commands.

It should also be well understood that the arrangements shown in FIGS. 1, 2, and 5 can be extended to multi-electrode arrays that comprise N×M working electrodes. In such an arrangement, the value of Vs can be the same for all working electrodes, or a different value of Vs can be used with each working electrode. Furthermore, each fluid compartment can contain a plurality of working electrodes, although this need not be the case. Moreover, each working electrode in a fluid compartment can be individually addressed for enablement/disablement, or enabled/disabled as a group such that the working electrodes in a given fluid compartment are either all enabled or all disabled.

Methods and apparati provided herein can be used to measure any electrochemically active analyte. Electrochemically active analytes that can be measured include, but are not limited to, metal ions, metallic compounds, amino acids, catecholamines, ascorbic acid, vitamin E, vitamin K, glutathione, ubiquinol, and the like. Electrochemically active analytes that can be measured also include, but are not limited to, certain peptides and metallopeptides.

Indirect assays where an immobilized substrate is associated with the working electrode and activated (i.e. converted into an electrochemically active analyte) by an agent of interest are also provided herein. An exemplary and non-limiting example of such indirect assays that can be conducted with the apparati and methods provided herein are electrode-attached redox-peptide systems that provide for kinetic characterization of protease agent activities on immobilized peptide substrates. Exemplary electrode-attached redox-peptide systems for kinetic characterization of the proteases thrombin and trypsin against immobilized peptide substrates have been described and can be adapted for use in the methods and apparati provided herein (Anne et al., *Langmuir,* 2012, 28 (23), pp 8804-8813). Another exemplary and non-limiting example of such indirect assays that can be conducted with the apparati and methods provided herein comprise assays for transfer of a redox-labeled phosphoryl group to surface-bound peptides that are substrates for protein kinase agent(s). Exemplary electrochemical assays for protein kinase catalyzed phosphorylations have been described and can be adapted for use in the methods and apparati provided herein (Martić et al., Analyst. 2011 Jan. 7; 136(1):107-12).

In certain embodiments, the methods and apparati provided herein can be used to measure analytes that are produced, consumed, and/or transformed by biologic processes. Such biological processes include, but are not limited to, activities of biological cells and in vitro activities of biological molecules. In certain embodiments, the activities of the biological cells or biological molecules are measured in compartments containing the biological cells or biological molecules. Biological cells that can be analyzed for various activities with the methods and apparati provided herein include, but are not limited to bacterial, yeast, fungal, insect, plant, and mammalian cells. In certain embodiments, a single biological cell is contacted by a working electrode. Biological processes that can be measured by methods and apparati provided herein include, but are not limited to, exocytosis, non-exocytotic release of a substance, ion-channel activity, ion-pump activity, uptake or transport of a substance into a cell, action potentials, and the like. In certain embodiments, a single biological cell is contacted by a working electrode and exocytosis is measured. In vitro activities of biological molecules that can be measured by methods and apparati provided herein include, but are not limited to, enzymatic, ion channel, ion pump, and receptor activities. Such enzymatic activities of biological molecules that can be measured by methods and apparati provided herein include, but are not limited to, kinase and protease activities. Such kinase activities that can be measured by methods and apparati provided herein include, but are not limited to, protein and lipid kinase activities. The methods and apparati provided herein can be used in methods to screen for or optimize compounds that modulate activities of biological cells and in vitro activities of biological molecules.

Analytes that are measured by methods and apparati provided herein can also be present or obtained from a biologic sample taken from a subject or taken from a processed biologic material. Subjects that yield biologic samples containing analytes of interest include, but are not limited to, humans, non-human animals, and plants. Processed biologic materials include but are not limited to, ground plant parts (i.e. seed, leaves, stems, roots, flowers), animal feed, food stuffs, fermentation products, fermentation broths, culture medias, and the like.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Materials and Methods Used in Exemplary Embodiments

Solutions and Cell Preparation:

The standard cell bath solution consisted of (in mM): 150 NaCl, 5 KCl, 5 $CaCl_2$, 2 $MgCl_2$, 10 HEPES, and 10 glucose, pH 7.2. We used a "high-$K^+$" solution to depolarize cells and trigger exocytosis that consisted of (in mM): 55 NaCl, 100 KCl, 5 $CaCl_2$, 2 $MgCl_2$, 10 HEPES, and 10 glucose, titrated to pH 7.2 with KOH. Electrodes were tested using cyclic voltammetry with a solution consisting of 1 mM $K_3Fe(CN)_6$ in 0.1 M KCl, pH 3.0 or 0.2 mM ferrocene carboxylic acid (FCA) in 150 mM NaCl and 10 mM HEPES, pH 7.2 or 0.5 mM FCA in 150 mM NaCl and 10 mM HEPES, pH 7.2 (as indicated in Results section).

Chromaffin cells were isolated from bovine adrenal glands as described previously (Yang et al. 2007). Cells were cultured in Hibernate A media with calcium (BrainBits LLC, Springfield, Ill., USA) in a refrigerator (4° C.) and used 1-6 days after isolation. In preparation for an experiment, cells were detached from the flask with a vigorous wash of culture media, then spun down at 100 g for 4 min. The supernatant was discarded and the cells were suspended and triturated in 5 ml standard bathing solution followed by a second pelleting. The supernatant was again discarded and the cells were re-suspended in 1 ml standard bathing solution resulting in a typical cell density of $\sim 2\times 10^6$ cells/ml. We loaded 500 of the cell solution on the microchip device and waited for 5 min to allow cell settling. We then vigorously washed the device with standard bathing solution twice to remove unattached cells. Exocytosis was triggered immediately following the wash by adding 100 μl of the "high-$K^+$" solution.

Device Fabrication:

Microscope slides (25×75×1 mm, Fisherbrand, Fisher Scientific, Pittsburgh, Pa., USA) were used as a transparent substrate and were cleaned by soaking in acetone for 5 min and then rinsed by methanol, isopropanol and DI water and then air dried. A Au film (~30 nm thick) was sputter deposited on top of a Ti adhesion layer (~2 nm thick).

The Au film was patterned using etching processes with S1813 photoresist (Rohm and Haas electronic materials, Philadelphia, Pa., USA) as the masking material. First, the conductor-coated slides were cleaned by sonication in acetone for 10 min followed by exposure to air plasma (PDC-32G, Harrick Scientific Corp., Pleasantville, N.Y., USA) for 1 min at medium RF power level. S1813 photoresist was then spin coated (Laurell Technologies Corp., North Wales, Pa., USA) onto the coated slide at 2500 rpm for 60 s to give a thickness of ~2 μm. The coated glass slide was then baked on a hot plate at 115° C. for 2 min. Then it was exposed to UV light through a high-resolution (20,000 dpi) transparency mask (CAD/Art services, Inc. Bandon, Oreg.) for about 43 s (NuArc 26-1KS Exposure unit, 1000 W metal halide lamp, 5.4 mW/$cm^2$) and then developed in M351 solution (Rohm and Haas electronic materials) for ~1 min. Au/Ti films were wet etched using Au etching reagent purchased from Sigma-Aldrich for ~5 s.

Following removal of the S1813 with acetone, the conductive films were patterned into 16 conductive traces with widths of 50 μm. Each trace leads to a 2 mm diameter pad at the edge of the chip to facilitate connection to a potentiostat.

The traces were insulated with photoresist (SU8 2025) except for 20 μm diameter openings and the connection pads. SU8 was first spin coated onto the device at 4000 rpm for 1 min to give a thickness of ~16 μm. Then it was baked on a hot plate at 65° C. for 3 min and then 95° C. for 5 min. The SU-8 was exposed through the photomask for ~33 s and baked again at 65° C. for 1 min and 95° C. for 5 min. Afterwards, it was developed in SU8 developer for ~10 min. Finally it was hard baked at 150° C. for 30 min to harden the film and seal cracks.

A polydimethylsiloxane (PDMS, Sylgard 184, Dow Corning, Midland, Mich., USA) gasket made with 1:20 mixing ratio was sealed onto the device to define the six fluid compartments. A custom-built chamber was used to hold the microchip device and to facilitate connection of the potentiostat to the pads at the edge of the chip. Ag/AgCl wires were used as the reference electrodes as described in the text.

Cleaning the working electrode was important to ensure an active surface. Before use, the device was rinsed with deionized water, air dried and then treated with air plasma at the medium power setting for 30 s to etch any photoresist residue on the electrode surface. For the chip insulated with SU8, a 10 min incubation in 25% $H_2O_2$/50 mM KOH was applied followed by rinse in deionized water rinse and air drying (Spégel, et al. 2007). Finally, a drop of solution containing 0.0025% poly (L-lysine) was applied to the electrode surface to aid in cell attachment to the electrode surface. Following the coating procedure, the device was thoroughly rinsed in deionized water and dried.

Amperometric Measurements:

Amperometric measurements were performed using an EPC9 amplifier (HEKA, Lambrecht, Germany). After connecting one of the conductive stripes to the amplifier headstage, the counter/reference Ag/AgCl electrode was placed into the cell bath solution. A potential of 600 mV was applied between the working electrode and the reference electrode. Then 50 μl of the cell suspension solution was loaded onto the chip for amperometric recordings. After waiting for 5 min for the suspended cells in the solution to fall into each individual microwell and settle down on the electrode surface, 50 μl of the high $K^+$ stimulation solution was then added to the reservoir. Amperometric signals were recorded at a bandwidth of 5 kHz and sampled at a rate of 20 ksamples/s. It was then further low-pass filtered with a cutoff frequency of 1 kHz by using $6^{th}$ order Bessel filter designed in Wavemetrics IFDL V4.0 (Wavemetrics, Lake Oswego, Oreg., USA).

Current Power Spectral Density (PSD) Measurement:

Current was measured using the EPC-10 two-electrode potentiostat (HEKA Electronik, Lambrecht, Germany). The current signal was low-pass filtered with a 4-pole Bessel filter set to a corner frequency of 5 kHz and sampled at 20 ksamples/s. The current power spectral density for 20 s of sampled data was calculated using Igor software (Wavemetrics, Inc., Lake Oswego, Oreg., USA). Data were processed with a segment length of 1024 samples and a square window to preserve low frequency information. In order to reduce line interference, devices were shielded and a Humbug instrument (Quest Scientific, North Vancouver, BC, Canada) was used in some experiments to remove 60 Hz and its harmonics from the signal. To further ensure the removal of line interference, a custom-developed Igor macro was applied to subtract 60 Hz and harmonics obtained from a training portion of the signal.

Example 2

Description of Prototype and the Principle of Operation

Figure 7:
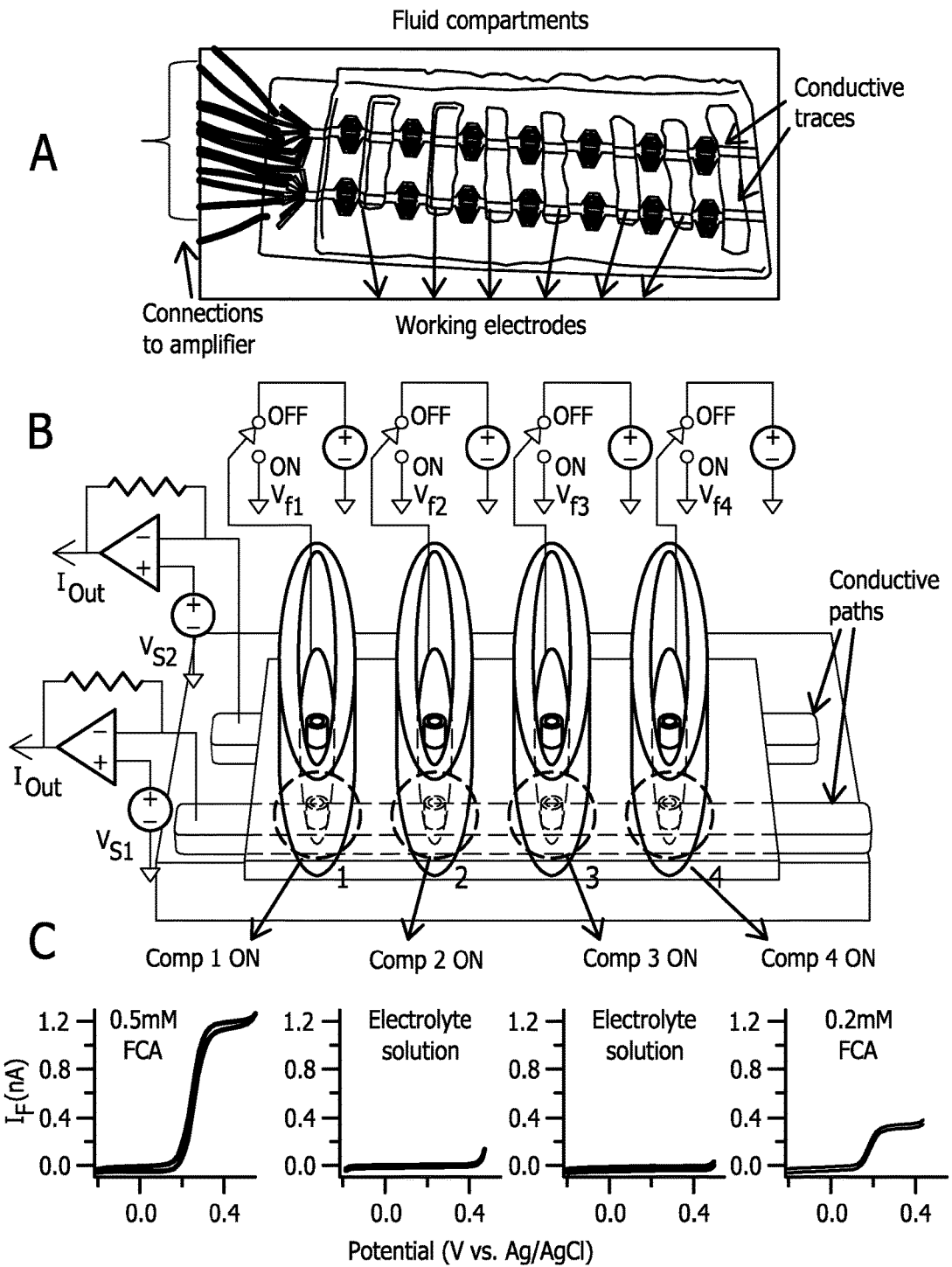
FIG. 7A, B, C illustrates: (A) a prototype multiplexed device with 6 fluid compartments and 16 conductive paths, where the conductive paths are insulated over most of their length, where the working electrodes are the small openings in the insulation with one working electrode in each fluid compartment for each conductive path, and working electrodes in a given conductive path use the op amplifier; (B) a schematic illustration of the principle of operation, where the top most electrodes are reference electrodes connected to voltage sources "Vf1", "Vf2", "Vf3", and "Vf4", the working electrodes are the disks (/cylinders) labelled 1, 2, 3, and 4 at the bottom of the fluid compartments driven to a voltage of Vs1 (relative to ground), where the reference and working electrodes are immersed in the fluid within the fluid compartment, and where the actual voltage drop at the surface of the working electrode is Vs-Vf; and (C) sample cyclic voltammograms (scan rate 10 mV/s) obtained from four fluid compartments containing FCA at the indicated concentrations or background electrolyte solution.

A prototype device to demonstrate the electrode addressing approach is depicted in FIG. 7(a) The prototype electrode arrays are fabricated using photolithography and wet etching processes as previously described (Liu et al. 2011). Sixteen conductive gold traces are patterned on a glass slide substrate. Most of the Au film is insulated with SU-8 photoresist whereas six ~20 μm-diameter openings are patterned in each trace with each opening serving as a working electrode residing in a separate fluid compartment. The six fluid compartments are fabricated by sealing a poly (dimethysiloxane) (PDMS) gasket on top of the device that contains six openings that are ~1 cm in diameter.

Individual electrodes are addressed by making a "row" connection (potentiostat connected to a conductive trace) and a "column" connection (fluid compartment selected with a Ag/AgCl reference electrode connected to ground). Working electrodes in inactive compartments can be "turned off" (disabled) in at least two exemplary ways. In the approach illustrated schematically in FIG. 7(b), inactive fluid-filled compartments contain Ag/AgCl reference electrodes that are set to the same potential as the working electrode ($V_s$) such that the potential difference between the working electrode and the electrolyte solution is zero. Alternatively, the potential of the reference electrode can be offset from $V_s$ so that the potential of the working electrodes in inactive fluid compartments is fixed to any desired value.

A second method for disabling inactive compartments is simply not to fill them with electrolyte solution. In this method different fluid compartments are selected by sequentially filling the active compartment with electrolyte solution and moving the ground/reference electrode to the active compartment.

Thus with the prototype device, 96 electrodes can be addressed with 16 row external connections plus either 1 or 6 reference electrodes. In general, if there are N row conductive traces and M fluid compartments, then N×M electrodes can be addressed with no more than N+M connections. For example, if N=16 electrodes are patterned in each well of a M=96-well plate, then 1536 electrodes can be addressed with either 17 connections if the reference electrode is moved (e.g., a Ag/AgCl wire) or with 112 external connections if reference electrodes are patterned for each fluid compartment.

For an initial test of the approach we perform cyclic voltammetry in four fluid compartments where the working electrode potential is scanned between −0.2 V and +0.5 V relative to a Ag/AgCl reference electrode using a potentiostat connected to one of the conductive traces. The first compartment contained 0.5 mM of the test analyte ferrocene carboxylic acid (FCA) whereas the second and third compartments contained only the background electrolyte solution and the fourth compartment contained 0.2 mM FCA. The cyclic voltammograms obtained upon sequentially activating each fluid compartment are depicted in lower part of FIG. 7(b).

According to Eq. 5.3.11 in (Bard and Faulkner 2001), for a disk electrode on an infinite insulating place, the diffusion-limited current ($I_{lim}$) for monovalent electron transfer is linearly proportional to the effective radius of the electrode. Assuming a diffusion coefficient for FCA of $5.4 \times 10^{-6}$ cm$^2$/s (Matsue et al. 1985), $I_{lim}$, is 1.04 nA in Compartment 1 and 0.41 nA in Compartment 4. Note that the faradaic currents in FIG. 7(b) are of the appropriate magnitude for the two compartments containing FCA whereas no faradaic currents are apparent when selecting the compartments with the background electrolyte solution.

Example 3

Noise of Amperometric Measurements

Ideally, amperometric measurements carried out using the multiplexing approach should be no higher in noise than recordings made from isolated electrodes without using multiplexing. In order to characterize amperometric noise we measure the current power spectral density ($S_I$) of electrochemical microelectrodes to understand how fluctuations in current vary with frequency.

Figure 8:
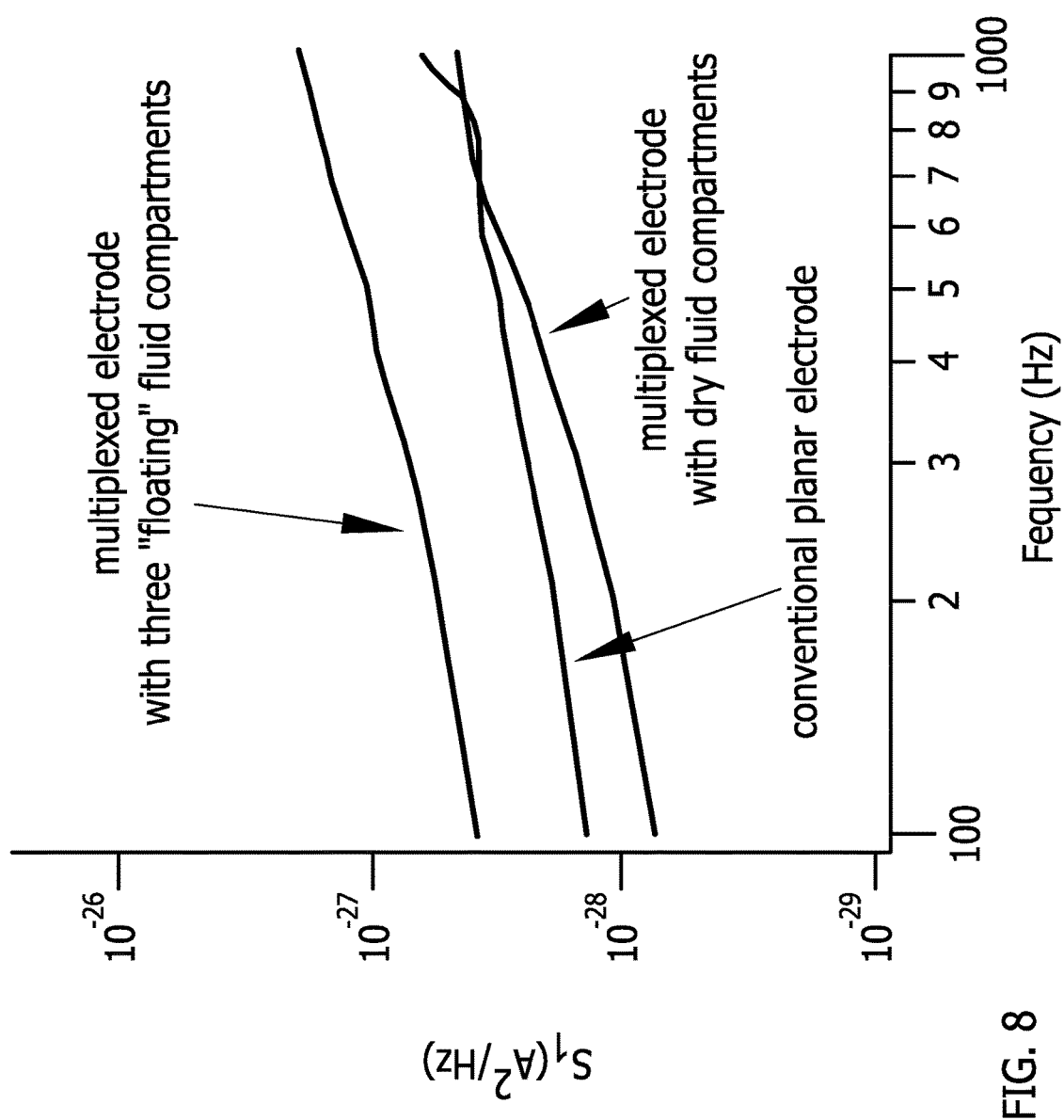
FIG. 8 illustrates that current noise power spectral density for an electrode on a multiplexing device is similar to that of an electrode fabricated in a single fluid compartment. However, if inactive compartments are filled with solution the noise increases even if the inactive compartments are not connected to ground (floating).

FIG. 8 demonstrates that the power spectral density of a 20 nm-diameter working electrode is essentially identical for the multiplexing approach compared to a conventional microchip electrode containing a single opening in the photoresist insulation if inactive compartments do not contain fluid. On the other hand, FIG. 8 demonstrates that the noise increases substantially when fluid was added to inactive compartments, even when these compartments are not connected to ground or $V_s$ (i.e., they are "floating"). We therefore carried out a set of experiments to understand why adding fluid to inactive compartments increases the current noise.

Figure 9A:
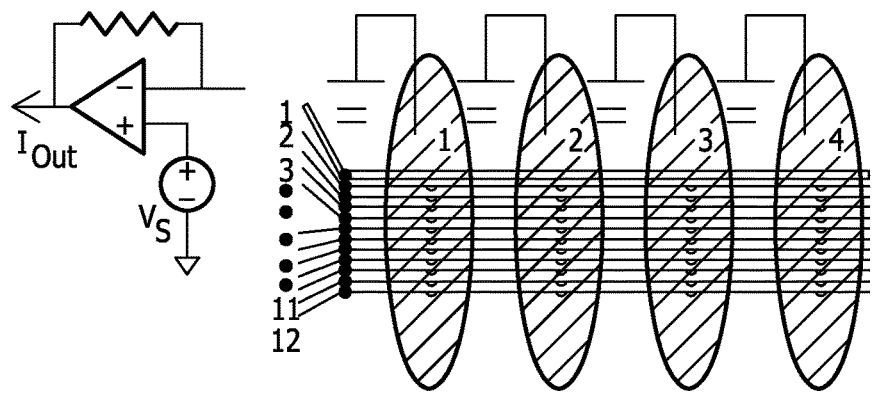
FIG. 9 illustrates that adding fluid to additional compartments leads to proportional increases in capacitance and noise whether or not the additional compartments are grounded. (a) Schematic of approach with additional compartments grounded or (b) Floating (c) The capacitance and noise power spectral density ($S_1$) increase linearly with the number of compartments containing fluid. The bottom chart plots $S_1$ normalized to capacitance to demonstrate that they increase in parallel upon fluid addition. Error bars are standard errors from measurements on n=7 floating electrodes and n=5 grounded electrodes.
Figure 9B:
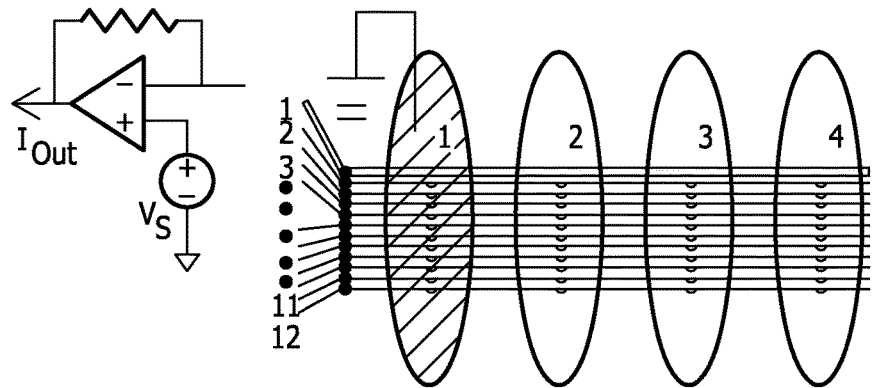
Figure 9C:
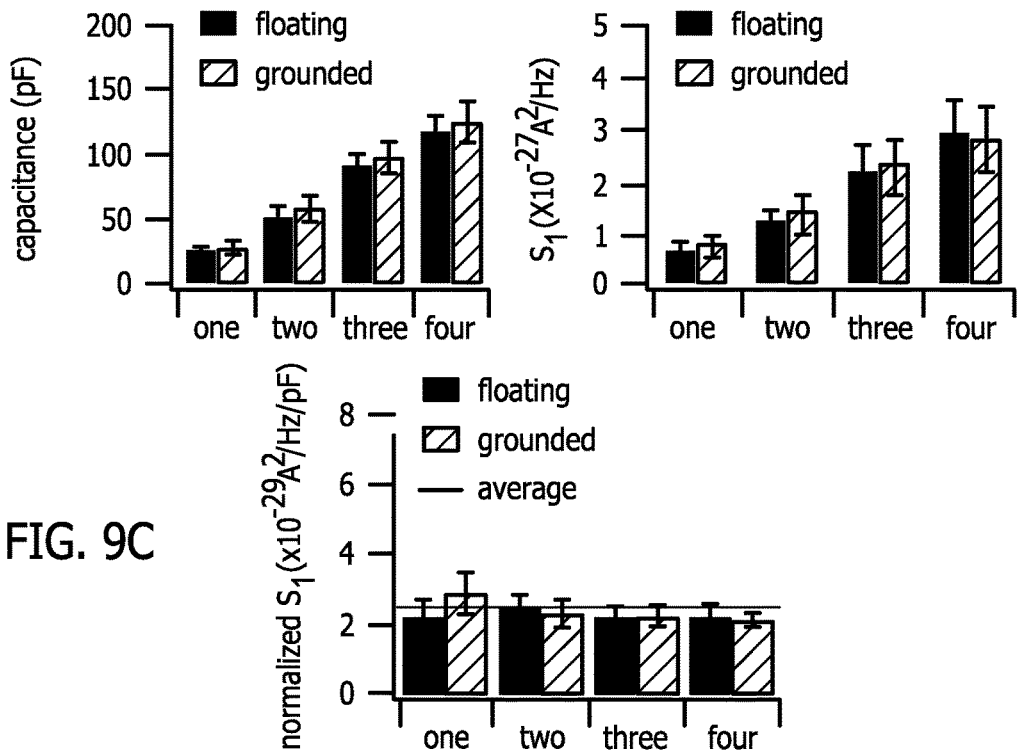

The current noise of electrochemical electrodes ($S_I$) is proportional to electrode area when carrying out amperometry (Hochstetler et al. 2000; Long and Weber 1988; Neher and Chow 1995; Yao and Gillis 2012). We measured the double-layer capacitance of a conductive path as a measure of the electrode area while varying the number of compartments that contained fluid. FIG. 9 demonstrates that the capacitance and noise ($S_f$) increase in proportion to the number of compartments containing electrolyte solution regardless of whether the additional compartments are connected to ground or left "floating".

Example 4

Analysis of the Equivalent Circuit Explains why Adding Fluid to Inactive Compartments Increases Measurement Noise Grounding multiple fluid compartments increases the capacitance and noise because the working electrode area increases in proportion to the number of electrodes on a conductive path that are electrically connected in parallel. On the other hand, there was not a clear explanation for the observations provided herein that fluid compartments lacking a direct connection to ground should contribute noise when they are filled with solution but not when they are dry.

The electrolyte solution in adjacent compartments will add capacitively coupled pathways to ground as depicted in schematic form in FIG. 10($a$). In order to understand how this affects measurements noise, we carried out an analysis of the equivalent circuit for the device. Current noise ($S_f$) is proportional to the capacitance, or more precisely, the admittance of the equivalent circuit (Hochstetler, et al. 2000; Long and Weber 1988; Neher and Chow 1995; Yao and Gillis 2012). FIG. 10 ($b$) depicts the equivalent circuit for a configuration of four conductive paths and three fluid compartments. Each rectangle represents the admittance ($Y_1$, inverse of impedance $Z_1$) of the interface between the electrode surface and the electrolyte solution in each fluid compartment.

Consider the case when all M compartments have fluid and only one "active" compartment is grounded with N electrodes in each compartment. The impedance of one conductive trace ($Z_{total}$) is given by:

$$Z_{total} = Z_1 \left\| \frac{\left(Z_1 + \frac{Z_1}{N-1}\right)}{(M-1)} \right\| \quad \text{(Eq. 1)}$$

Resulting in a total admittance given by:

$$Y_{total} = Y_1 \left[1 + \frac{(M-1)(N-1)}{N}\right] \quad \text{(Eq. 2)}$$

If $N$ is large, $$Y_{total} \approx MY_1 \quad \text{(Eq. 3)}$$

Figure 11A:
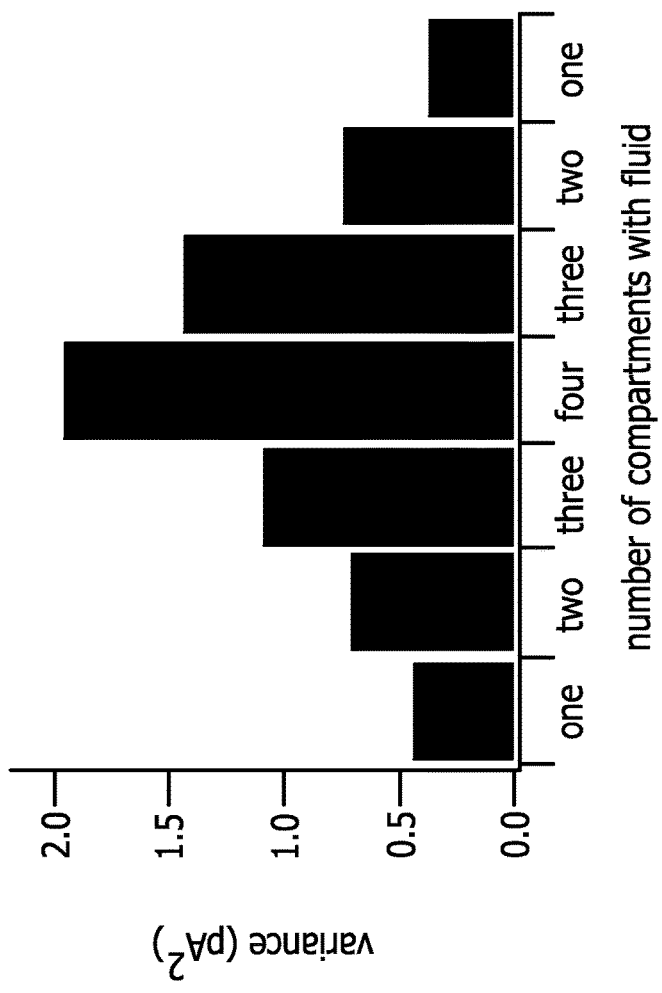
FIG. 11 illustrates that the noise increase that results upon addition of fluid to multiple compartments can be reversed by removing the fluid. Following removal of electrolyte solution, each well was washed with distilled water and dried with compressed air. (a) Variance of the current increases with solution addition in more compartments and decreases with solution removal. (b) Current noise level from the working electrode after solution addition and removal remains similar to original noise level.
Figure 11B:

Therefore, the total admittance, and thus noise, is proportional to the number of fluid-filled compartments when each compartment contains many electrodes and all compartments are enabled. In such cases, low noise can be obtained by filling one compartment at a time with fluid. Sequential recordings are then carried out by adding fluid to each compartment while removing fluid from previously used compartments. FIG. 11 demonstrates that removing the fluid can reverse the noise increase that occurs upon addition of fluid to multiple compartments.

Figure 13:
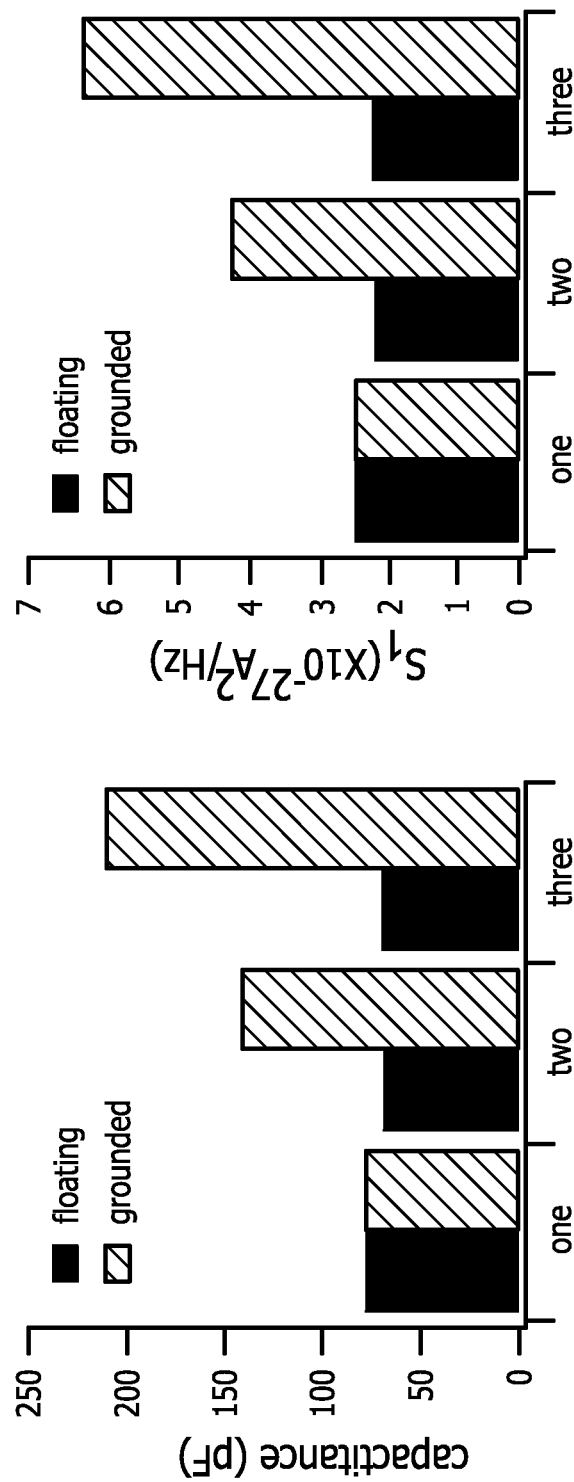
FIG. 13 illustrates that adding fluid to multiple compartments does not increase the noise if each compartment only contains one electrode and only one fluid compartment is connected to ground. As predicted by Eq. 2, for a single conductive trace (i.e., one electrode per fluid compartment, N=1), the admittance/capacitance and noise will not increase as fluid is added to additional fluid compartments if they are left "floating" (filled bars, M=1, 2 or 3) because there is no capacitively coupled pathway to ground (contrast with FIG. 3c with N=16 conductive traces). On the other hand, connecting multiple fluid compartments to ground increases the effective electrode area and thus increases the capacitance and noise (hatched bars).

In contrast, Eq. 8 predicts that adding fluid to multiple compartments will not increase capacitance and noise if each compartment contains a single electrode (N=1) and the additional fluid compartments are left floating. The data of FIG. 13 are in agreement with this prediction and thus support the validity of the analyses of Eqs. 1 and 2.

Example 5

Figure 12:
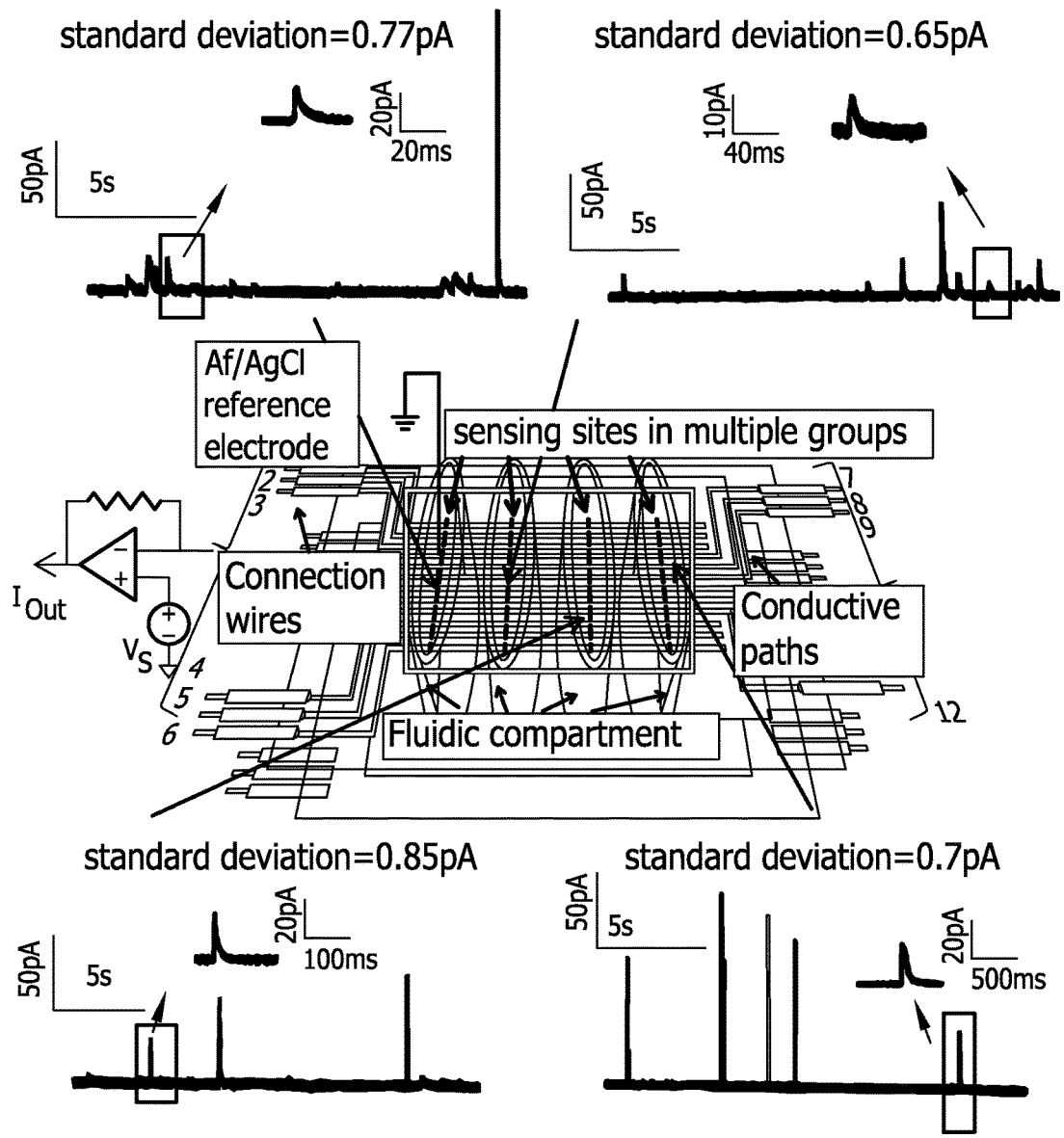
FIG. 12 illustrates sequential amperometric recordings of quantal exocytosis from a single trace with cells sequentially placed in each of four fluid compartments.

Application of Multiplexing Approach to Record Quantal Exocytosis from Chromaffin Cells Neurons and neuroendocrine cells release transmitter by the process of exocytosis as vesicles laden with transmitter fuse with the cell membrane and release their contents into the extracellular space. If an electrochemical microelectrode is located immediately adjacent to a cell, then exocytosis of readily oxidized transmitter such as catecholamine can be detected. In fact, single-vesicle fusion events ("quantal" exocytosis) can be recorded as the vesicle contents are oxidized on the electrode surface to produce spikes of current during amperometric recordings (Chow et al. 1992; Wightman et al. 1991). Our group and others are developing arrays of electrochemical microelectrodes to facilitate high-throughput measurement of quantal exocytosis (Amatore, et al. 2007; Amatore, et al. 2006; Barizuddin, et al. 2010; Berberian, et al. 2009; Chen, et al. 2003; Chen, et al. 2007; Dias, et al. 2002; Dittami and Rabbitt 2010; Gao, et al. 2009; Gao, et al. 2008; Hafez, et al. 2005; Liu, et al. 2011; Sen, et al. 2009; Spégel, et al. 2007; Spégel, et al. 2008; Sun and Gillis 2006). Therefore we applied the proposed multiplexing approach to record quantal exocytosis from bovine adrenal chromaffin cells. FIG. 12 demonstrates that the multiplexing approach can be used to record quantal exocytosis sequentially from four cells placed in four fluid compartments using a single conductive trace/potentiostat. Amperometric recordings of exocytosis were carried out while holding the working electrode at a potential of +0.6 V relative to the Ag/AgCl reference electrode. Spikes of amperometric current result from the release of catecholamines upon exocytosis of individual secretory granules are identified by their characteristic time course and area and were not observed before depolarizing cells with a high $K^+$ solution or when the electrode was held at 0 V (data not shown). The noise (current standard deviation) of each recording ranged from 0.65 to 0.85 pA for a bandwidth of 1 kHz, which is comparable to the noise measured from individual electrode with a diameter of 20 µm (Liu, et al. 2011).

CITED REFERENCES

C. Amatore, S. Arbault, I. Bonifas, M. Guille, F. Lemaître and Y. Verchier, Biophysical Chemistry 129, 181-189 (2007)

C. Amatore, S. Arbault, Y. Chen, C. Crozatier, F. Lemaître and Y. Verchier, Angewandte Chemie—International Edition 45, 4000-4003 (2006)

A. J. Bard and L. R. Faulkner, Electrochemical Methods: Fundamentals and Applications. (Wiley & Sons, New York, 2001)

S. Barizuddin, X. Liu, J. C. Mathai, M. Hossain, K. D. Gillis and S. Gangopadhyay, ACS Chemical Neuroscience 1, 590-597 (2010)

K. Berberian, K. Kisler, F. Qinghua and M. Lindau, Analytical Chemistry 81, 8734-8740 (2009)

P. Chen, B. Xu, N. Tokranova, X. Feng, J. Castracane and K. D. Gillis, Analytical Chemistry 75, 518-524 (2003)

X. Chen, Y. Gao, M. Hossain, S. Gangopadhyay and K. D. Gillis, Lab on a Chip—Miniaturisation for Chemistry and Biology 8, 161-169 (2007)

R. H. Chow, L. von Ruden and E. Neher, Nature 356, 60-3 (1992)

A. F. Dias, G. Dernick, V. Valero, M. G. Yong, C. D. James, H. G. Craighead and M. Lindau, Nanotechnology 13, 285-289 (2002)

G. M. Dittami and R. D. Rabbitt, Lab on a Chip—Miniaturisation for Chemistry and Biology 10, 30-35 (2010)

G. C. Fiaccabrino, M. Koudelka-Hep, S. Jeanneret, A. van den Berg and N. F. de Rooij, Sensors and Actuators: B. Chemical 19, 675-677 (1994)

Y. Gao, S. Bhattacharya, X. Chen, S. Barizuddin, S. Gangopadhyay and K. D. Gillis, Lab on a Chip—Miniaturisation for Chemistry and Biology 9, 3442-3446 (2009)

Y. Gao, X. Chen, S. Gupta, K. D. Gillis and S. Gangopadhyay, Biomedical Microdevices 10, 623-629 (2008)

I. Hafez, K. Kisler, K. Berberian, G. Dernick, V. Valero, M. G. Yong, H. G. Craighead and M. Lindau, Proceedings of the National Academy of Sciences of the United States of America 102, 13879-13884 (2005)

S. E. Hochstetler, M. Puopolo, S. Gustincich, E. Raviola and R. M. Wightman, Analytical Chemistry 72, 489-496 (2000)

K. Ino, W. Saito, M. Koide, T. Umemura, H. Shiku and T. Matsue, Lab on a Chip—Miniaturisation for Chemistry and Biology 11, 385-388 (2011)

X. Liu, S. Barizuddin, W. Shin, C. J. Mathai, S. Gangopadhyay and K. D. Gillis, Analytical Chemistry 83, 2445-2451 (2011)

X. Liu, S. Barizuddin, W. Shin, C. J. Mathai, S. Gangopadhyay and K. D. Gillis, Anal Chem 83, 2445-51 (2011)

J. T. Long and S. G. Weber, Analytical Chemistry 60, 2309-2311 (1988)

T. Matsue, D. H. Evans, T. Osa and N. Kobayashi, Journal of the American Chemical Society 107, 3411-3417 (1985)

E. Neher and R. H. Chow, Bioelectrochemistry and Bioenergetics 38, 251-253 (1995)

J. Pei, M. L. Tercier-Waeber, J. Buffle, G. C. Flaccabrino and M. Koudelka-Hep, Analytical Chemistry 73, 2273-2281 (2001)

A. Sen, S. Barizuddin, M. Hossain, L. Polo-Parada, K. D. Gillis and S. Gangopadhyay, Biomaterials 30, 1604-12 (2009)

C. Spégel, A. Heiskanen, J. Acklid, A. Wolff, R. Taboryski, J. Emnéus and T. Ruzgas, Electroanalysis 19, 263-271 (2007)

C. Spégel, A. Heiskanen, S. Pedersen, J. Emnéus, T. Ruzgas and R. Taboryski, Lab on a Chip—Miniaturisation for Chemistry and Biology 8, 323-329 (2008)

X. Sun and K. D. Gillis, Analytical Chemistry 78, 2521-2525 (2006)

R. M. Wightman, J. A. Jankowski, R. T. Kennedy, K. T. Kawagoe, T. J. Schroeder, D. J. Leszczyszyn, J. A. Near, E. J. Diliberto Jr and O. H. Viveros, Proceedings of the National Academy of Sciences of the United States of America 88, 10754-10758 (1991)

M. S. Wilson and W. Nie, Analytical Chemistry 78, 6476-6483 (2006)

Y. Yang, T. J. Craig, X. Chen, L. F. Ciufo, M. Takahashi, A. Morgan and K. D. Gillis, J Gen Physiol 129, 233-44 (2007)

J. Yao and K. D. Gillis, Analyst 137, 2674-81 (2012)

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for measuring a signal corresponding to a characteristic of a fluid using an electrode array, the electrode array comprising (1) a first working electrode, wherein the first working electrode is located in a first compartment that contains the fluid and is in contact with the fluid, (2) a first reference electrode, wherein the first reference electrode is located in the first compartment and is in contact with the fluid but not the first working electrode, (3) a second working electrode, wherein the second working electrode is located in a second compartment that contains the fluid and is in contact with the fluid, and (4) a second reference electrode, wherein the second reference electrode is located in the second compartment and is in contact with the fluid but not the second working electrode, the method comprising:

enabling the first working electrode of the electrode array by controlling a first voltage potential relationship between the enabled first working electrode and the first reference electrode, while the first working electrode is enabled, disabling the second working electrode of the electrode array by controlling a second voltage potential relationship between the disabled second working electrode and the second reference electrode; and measuring a signal produced by the enabled first working electrode while the second working electrode is disabled, the measured signal corresponding to a characteristic of the fluid in the first compartment.

2. The method of claim 1 wherein the electrode array comprises a plurality of additional working electrodes and additional reference electrodes that are located in a plurality of additional compartments that contain the fluid, wherein the disabling step comprises:

while the first working electrode is enabled, disabling a plurality of the additional working electrodes of the electrode array by controlling a plurality of the second voltage relationships between the disabled additional working electrodes and the additional reference electrodes that share the same additional compartments as the disabled additional working electrodes.

3. The method of claim 2 wherein the disabling step further comprises:

while the first working electrode is enabled, disabling all of the additional working electrodes of the electrode array that share the same additional compartments as the disabled additional working electrodes.

4. The method of claim 1 further comprising repeating the enabling step, the disabling step, and the measuring step while using a different working electrode of the electrode array as the first working electrode.

5. The method of claim 4 wherein the first working electrode is at a first voltage potential, and wherein the enabling step comprises connecting the first fluid-containing compartment in which the first working electrode is located to a second voltage potential via the first reference electrode that is located in the same compartment as the first working electrode, wherein the controlled first voltage potential relationship is based on the first voltage potential and the second voltage potential and causes a current to flow through the fluid in the first fluid-containing compartment via the first working electrode.

6. The method of claim 5 wherein the second voltage potential is ground voltage.

7. The method of claim 5 wherein the disabling step comprises:
while the first working electrode is enabled, connecting the second fluid-containing compartment to a third voltage potential via the second reference electrode that is located in the same compartment as the second working electrode, wherein the controlled second voltage potential relationship is based on the first voltage potential and the third voltage potential and prevents an appreciable current from flowing through the fluid in the second fluid-containing compartment via the disabled second working electrode.

8. The method of claim 7 wherein the third voltage potential is substantially equal to the first voltage potential.

9. The method of claim 7 wherein the third voltage potential is sufficient to prevent a reaction by the fluid in the second fluid-containing compartment.

10. The method of claim 7 wherein the third voltage potential is sufficient to cause a reaction by the fluid in the second fluid-containing compartment.

11. The method of claim 5 further comprising varying the first voltage potential over time.

12. The method of claim 1 further comprising:
filling a plurality of the compartments with the fluid; and
performing the enabling step, the disabling step, and the measuring step while the compartments are filled with the fluid.

13. The method of claim 12 wherein the fluid comprises a plurality of different fluids, and wherein the filling step comprises filling at least one of the compartments with a first fluid and filling at least one of another of the compartments with a second fluid.

14. The method of claim 1 wherein the disabling step comprises disabling all of the working electrodes of the electrode array other than the first working electrode.

15. The method of claim 1 wherein the first working electrode comprises only one working electrode of the electrode array.

16. The method of claim 1 wherein each of at least a plurality of the compartments further contain a plurality of the working electrodes of the electrode array.

17. The method of claim 1 further comprising repeating the enabling step, the disabling applying step, and the measuring step while using a different working electrode of the electrode array as the first working electrode until all of the working electrodes have been used as the first working electrode.

* * * * *